United States Patent
Lianidou et al.

(10) Patent No.: US 12,391,985 B2
(45) Date of Patent: Aug. 19, 2025

(54) METHOD OF DETERMINING PIK3CA MUTATIONAL STATUS IN A SAMPLE

(71) Applicant: PHARMASSIST LTD, Athens (GR)

(72) Inventors: Evrykleia Lianidou, Athens (GR); Athina Markou, Athens (GR)

(73) Assignee: PHARMASSIST LTD, Athens (GR)

(*) Notice: Subject to any disclaimer, the term of this patent is extended or adjusted under 35 U.S.C. 154(b) by 822 days.

(21) Appl. No.: 17/699,761

(22) Filed: Mar. 21, 2022

(65) Prior Publication Data

US 2022/0298565 A1 Sep. 22, 2022

Related U.S. Application Data

(63) Continuation-in-part of application No. 15/501,457, filed as application No. PCT/GR2015/000036 on Jul. 28, 2015, now Pat. No. 11,279,979.

(60) Provisional application No. 62/034,231, filed on Aug. 7, 2014.

(51) Int. Cl.
| | |
|---|---|
| C12Q 1/6858 | (2018.01) |
| C12Q 1/6816 | (2018.01) |
| C12Q 1/6853 | (2018.01) |
| C12Q 1/6886 | (2018.01) |

(52) U.S. Cl.
CPC ......... *C12Q 1/6858* (2013.01); *C12Q 1/6816* (2013.01); *C12Q 1/6853* (2013.01); *C12Q 1/6886* (2013.01); *C12Q 2600/106* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 8,026,053 B2 | 9/2011 | Samuels et al. |
| 8,901,285 B2 | 12/2014 | Board et al. |
| 8,980,556 B2 | 3/2015 | Buettner et al. |
| 9,169,514 B2 | 10/2015 | Jia et al. |
| 9,228,239 B2 | 1/2016 | Buettner et al. |
| 9,512,482 B2 | 12/2016 | Princen et al. |
| 9,556,475 B2 | 1/2017 | Regan et al. |
| 2008/0268449 A1 | 10/2008 | Hoon |
| 2009/0208505 A1 | 8/2009 | Samuels et al. |
| 2010/0041048 A1 | 2/2010 | Diehl et al. |
| 2011/0027779 A1 | 2/2011 | Board et al. |
| 2011/0312523 A1 | 12/2011 | Xu et al. |
| 2011/0319477 A1 | 12/2011 | Samuels et al. |
| 2013/0078631 A1 | 3/2013 | Komori |
| 2014/0017682 A1 | 1/2014 | Buettner et al. |
| 2014/0024033 A1 | 1/2014 | Jia et al. |
| 2014/0100121 A1 | 4/2014 | Lo et al. |
| 2014/0141425 A1 | 5/2014 | Board et al. |
| 2014/0248612 A1 | 9/2014 | Princen et al. |
| 2015/0079593 A1 | 3/2015 | Samuels et al. |
| 2015/0152510 A1 | 6/2015 | Buettner et al. |
| 2016/0032408 A1 | 2/2016 | Board et al. |
| 2016/0040242 A1 | 2/2016 | Jia et al. |
| 2016/0040255 A1 | 2/2016 | Board et al. |
| 2016/0083804 A1 | 3/2016 | Buettner et al. |

FOREIGN PATENT DOCUMENTS

| | | |
|---|---|---|
| CN | 102234685 A | 11/2011 |
| CN | 102533958 A | 7/2012 |
| EP | 2377933 A1 | 10/2011 |
| EP | 2505672 A1 | 10/2012 |
| EP | 2574680 A1 | 4/2013 |
| EP | 2711432 A1 | 3/2014 |
| WO | 2005/091849 A2 | 10/2005 |
| WO | 2009019008 A1 | 2/2009 |
| WO | 2009040557 A2 | 4/2009 |
| WO | 2011/131151 A1 | 10/2011 |
| WO | 2012/75231 A1 | 6/2012 |

(Continued)

OTHER PUBLICATIONS

Zhou (Biotechniques vol. 50 pp. 311-318 May 2011).*
Zhou Luming et al: "Rare allele enrichment and detection by allele-specific PCR, competitive probe blocking, and melting analysis", Biotechniques, Informa Healthcare, US, vol. 50, No. 5, May 1, 2011 (May 1, 2011), pp. 311-318, XP009166284, ISSN: 0736-6205.
International Search Report and Written Opinion of the ISA for PCT/GR2015/000036, ISA/EP, Rijswijk, NL, mailed Dec. 3, 2015.
Samuels (Science vol. 304 Apr. 23, 2004 pp. 554-555).
Helen Schneck, et al.; Analysing the mutational status of PIK3CA in circulating tumor cells from metastatic breast cancer patients; Molecular Oncology, vol. 7, No. 5, 2013, p. 976-986.
European Search Report dated Jun. 12, 2018.

(Continued)

*Primary Examiner* — Amanda Haney
(74) *Attorney, Agent, or Firm* — Harness, Dickey & Pierce, P.L.C.

(57) ABSTRACT

An ultra-sensitive, specific methodology for detecting PIK3CA mutations in biological samples of cancer patients, comprises a combination of allele-specific, asymmetric rapid PCR and melting analysis in a DNA sample from Circulating Tumor Cells, cell-free DNA in plasma/serum, or Formalin-Fixed Paraffin-Embedded tissues. Using the allele-specific primers for hotspot mutations in exons 9 and 20 (E545K and H1047R), detection can enhance amplification of mutant PIK3CA allele sequence, whereas presence of corresponding competitive blocking unlabeled probes for each exon can avoid non-specific amplification of wild-type PIK3CA sequence increasing the sensitivity and the specificity of method. The mutational detection is completed with melting curve analysis of the unlabeled probe and DNA template of the mutant PIK3CA sequence. Evaluation of PIK3CA mutational status on CTC in peripheral blood and cfDNA in plasma/serum of patients has potential for clinical applications and therapeutic interventions, since presence of PIK3CA mutations is associated with response to molecular targeted therapies.

14 Claims, 19 Drawing Sheets

Specification includes a Sequence Listing.

(56) References Cited

FOREIGN PATENT DOCUMENTS

| WO | 2012/095378 | A1 | 7/2012 |
| WO | 2012151560 | A2 | 11/2012 |
| WO | 2013026027 | A1 | 2/2013 |

OTHER PUBLICATIONS

International Preliminary Report on Patentability for PCT/GR2015/000036 with annexes, ISA/EP, Riiswiik, NL, mailed Sep. 19, 2016.
Crowley (Nature Aug. 2013 vol 10 pp. 472-484).

* cited by examiner

EXON 9-PIK3CA

A: mutation site

G: additional mismatch is presented by italics

Primers (forward and reverse) are in bold underlined

Unlabeled blocking probe is presented in bold

EXON 9 SEQUENCE:

<u>AGTAACAGACTAGCTAGAGACAATGAATTAAGGGAAAATGACAAAGAACAGCTCAAAGC</u>
<u>AATTTCTACACGAGA</u>TCCCTCTCTGAAATCACTAAG*A*GGAGAAAGA<u>TTTTCTATGGA</u>
<u>GTCACAG</u>

FIG. 7

EXON 20-PIK3CA

G: mutation site

Primers (forward and reverse) are in bold underlined

Unlabeled blocking probe is presented in bold

EXON 20 SEQUENCE:

GTTTCAGGAGATGTGTTACAAGGCTTATCTAGCTTATTCGAGAGCATGCCAATCTCTTCATA
AATCTTTTCTCAATGATGCTTGGCTCTGGAATGCCAGAACTACAATCTTTTGATGACATTG
CATACATTCGAAAGACCCTAGCCCTTAGATAAAACTGAGCAAGAGGCTTTGGAGTATTTCAT
GAAACAAATGAATGATGCACGTCATGGTGGCTGGACAACAAAAATGGATTGCATCTTCCAC
ACAATTAAACAGCATGCATTGAACTGAAAAGATAACTGAGAAAATGAAAGCTCACTCTGGA
TTCCACACTGCACTGTTAATAACTCTCAGCAGCCAAAGACCGATTGCATAGGAATTGCACA
ATCCATGAACAGCATTAGAATTTACAGCAAGACAGAAATAAAATACTATATAATTTAAAT
AATGTAAAACGCAAACAGGGTTTGATAGCACTTAAACTAGTTCATTTCAAAATTAAGCTTTA
GAATAATGCGCAATTTCATGTTATGCCTTAAGTCCAAAAAGGTAAACTTTTGAAGATTGTTT
GTATCTTTTTAAAAACAAAACAAAATCCCCAAAATATATAGAAATGATGGAG
AAGGAAAAA

FIG. 7 (CONTINUE)

METHOD OF DETERMINING *PIK3CA* MUTATIONAL STATUS IN A SAMPLE

SEQUENCE LISTING

This application contains references to amino acid sequences and/or nucleic acid sequences which have been submitted concurrently herewith as the sequence listing text file entitled "1775801COA_seq_listing.TXT", file size 4.2 KiloBytes (KB), created on Feb. 9, 2022. The aforementioned sequence listing is hereby incorporated by reference in its entirety pursuant to 37 C.F.R. § 1.52(e)(5).

TECHNICAL FIELD

The present invention relates to a highly sensitive method for determining PIK3CA mutational status in a DNA sample of, for example, circulating tumor cells (CTCs), cell-free DNA (cfDNA) in plasma/serum and formalin-fixed paraffin-embedded (FFPE) tissues.

BACKGROUND OF THE INVENTION

Circulating tumor cells (CTC) detection and enumeration can serve as a "liquid biopsy" and an early marker of response to systemic therapy, while their molecular characterization has a strong potential to be translated to individualized targeted treatments and spare cancer patients unnecessary and ineffective therapies.

It has been shown that detection of one or more CTCs in 7.5 mL of blood before adjuvant chemotherapy can accurately predict overall survival (OS). Persistent detection of CTCs during the first 5 years of follow-up was associated with an increased risk of late disease relapse and death and indicates the presence of chemo- and hormone therapy—resistant residual disease. A recent prospective clinical study confirmed that the presence of one or more CTCs predicted for early recurrence and decreased overall survival (OS).

In metastatic breast cancer (MBC), CTCs represent an independent prognostic factor for progression-free survival (PFS) and OS, and the CTC enumeration assay (Cell-Search™ system, Veridex) was cleared by FDA for metastatic breast, prostate, and colorectal cancer. Increased numbers of CTCs before the second cycle of therapy was an early predictive marker of poor PFS and OS, and could be used to monitor treatment benefit, whereas CTCs decrease under treatment was stronger with targeted therapy. The detection of CTCs in patients with MBC before front-line therapy could define a subgroup of patients with dismal clinical outcome.

It is now established that cell-free DNA (cfDNA) is released to the circulation from cells undergoing apoptosis or other physiological events induced by micro-environmental stress and can be identified in the blood samples of patients with cancer. However, related to the length of the produced cfDNA fragments (DNA integrity), the source of cfDNA can be distinguished from the apoptotic or necrotic origin. The term circulating tumor DNA (ctDNA), comprises essentially a subtype of total cfDNA that is derived from the tumor. Many studies have shown that both ctDNA and CTCs are present in plasma/serum and peripheral blood of cancer patients not only in advanced but even at the early stages.

Although there are many commercially available cfDNA extraction kits, the efficiency and yield are still low due to loss of starting material during extraction, and its quantification is variable because of a lack of standardization. Nevertheless, the efficiency of cfDNA extraction can directly impact the outcome of mutation detection i.e., assay sensitivity.

Phosphoinositide 3-kinases (PI3Ks) comprise a family of lipid kinases, discovered in the 1980s, that are responsible for mediating important biological functions such as cell survival, differentiation and proliferation. The phosphatidylinositol 3-kinase (PI3K)/AKT signaling pathway is implicated in human diseases including cancer, and understanding the intricacies of this pathway may provide new avenues for therapeutic intervention. Somatic mutations in the p110a catalytic subunit of PI3K, are very frequent in many types of solid cancers such as breast, colorectal, prostate, ovarian, cervical, head and neck, esophageal, lung, brain, skin, liver, pancreatic, gastric or thyroid cancer and play a crucial role in response to molecular target therapies and often co-occur with HER-2 amplification in breast cancer. The mutations of PIK3CA have been reported in 18%-40% of breast cancer patients, while the vast majority, comprising approximately 90% of cases, is clustered at two hot-spot regions in exon 9 and exon 20.

The clinical relevance of detecting PIK3CA hotspot mutations in a DNA sample of CTCs, cfDNA or FFPE tissues is very important, as the presence of PIK3CA mutations is associated with drug resistance in targeted therapies. The problem is that mutations are present in very low amounts in clinical tumor samples and the detection limits of the existing methodologies are very low, thus leading to false negative that may impact clinical diagnosis and patient management.

Analysis of ctDNA has been shown as a useful tool in order to assess tumor progression and to evaluate prognosis, diagnosis and response to treatment. Many studies have confirmed the clinical utility of ctDNA and many technologies have been developed in order to increase the analytical sensitivity of the methodologies used for this purpose. Janku et al., using the beaming method, have shown that the concordance proportion between tissues and plasma for PIK3CA mutations in both exons was 91% [Janku F, et al. Actionable mutations in plasma cell-free DNA in patients with advanced cancers referred for experimental targeted therapies. Oncotarget. 2015; 6:12809-21], In another study, the percentage of PIK3CA mutations in ctDNA using a digital PCR (dPCR) assay was found in 22.7% of the patients with breast cancer [Oshiro C, et al. PIK3CA mutations in serum DNA are predictive of recurrence in primary breast cancer patients. Breast Cancer Res Treat. 2015; 150:299-307], For this reason, a novel method for PIK3CA hotspot mutations has been developed, characterized by extreme sensitivity (0.05%) and high specificity (100%) [Markou A, et al. PIK3CA mutational status in circulating tumor cells can change during disease recurrence or progression in patients with breast cancer. Clin Cancer Res. 2014 Nov. 15; 20(22):5823-34]. This assay offers many advantages: it can detect very low amounts of mutant alleles with PIK3CA mutations in presence of an excess of the wild type alleles. Moreover, by using the developed method, PIK3CA mutations in DNA isolated from CTCs could be detected at a much higher percentage both in early breast cancer patients (20.3%) and in patients with clinically confirmed metastasis (35.1%) than reported before.

For this reason, an ultrasensitive and highly specific methodology for the detection of PIK3CA hotspot mutations (exons 9 and 20) in CTCs, based on the combination of allele specific priming, competitive blocking probe of wild-type amplification, asymmetric PCR, and probe melting analysis

[Markou A, et al. PIK3CA mutational status in circulating tumor cells can change during disease recurrence or progression in patients with breast cancer. Clin Cancer Res. 2014 Nov. 15; 20(22):5823-34] was developed and validated. Data also suggest that PIK3CA mutational status can change during disease recurrence or progression in patients with breast cancer and that the presence of PIK3CA mutations in CTC is associated with worse survival in patients with clinically confirmed metastasis [Markou A, et al. PIK3CA mutational status in CTCs can change during disease recurrence or progression in patients with breast cancer. Clin Cancer Res. 2014 Nov. 15; 20(22):5823-34].

SUMMARY

It is an object to provide an improved method for determining PIK3CA mutational status in a sample of, for example, CTCs.

This object is wholly or partially achieved by a method according to claim 1. Embodiments and further details of the invention are set forth in the appended dependent claims, in the drawings and in the sequence listing.

Thus, the method relates to determining the presence a PIK3CA allele a sample, i.e. a PIK3CA allele containing a mutation (-s) such as a hot spot mutation (-s) in a sample. The sample may, for example, be of CTCs but the method may also be used in any other types of biological samples, e.g., in cell-free DNA in plasma/serum or FFPE tissues in solid tumors. The detection of PIK3CA mutation (-s) may be used to determine many types of cancers including cancers of the colon, breast, brain, thyroid, pancreatic, prostate, head and neck, ovarian, cervical, liver, stomach, esophageal, skin and lung. The method is especially advantageous when determining risks of developing cancer where PIK3CA mutations could be present such as e.g., during early diagnosis of breast cancer.

The inventive method is based on an approach that was first described for BRAF mutations by L. Zhou et al. [Zhou L, et al. Rare allele enrichment and detection by allele-specific PCR, competitive probe blocking, and melting analysis. BioTechniques 2011; 50:311-8]. Using the basic approach of this method, de novo primers and probes were designed and all the experimental conditions were checked in order to detect PIK3CA hotspot mutations in a sample of CTCs. Aspects of melting analysis and unlabeled probes were licensed from the University of Utah to IDAHO technology.

The method according to the invention can enhance rare allele detection in a homogeneous system. The method comprises an asymmetric and allele specific Polymerase Chain Reaction (PCR) using competitive blocking probe, and a melting analysis. The method requires a mutant allele specific primer complementary to the 3' (three prime) end of the first strand of the mutant allele DNA target to be amplified and an unlabeled blocking probe (competitive probe), which is an oligonucleotide complementary to the wild type sequence of the corresponding first strand of wild type DNA and exactly at the position in which the mutation to be detected is present. Furthermore, the method includes a common primer that is complementary to the 3' end of the second strand of the DNA target to be amplified by the PCR.

The method according to the invention for determining the presence of a PIK3CA mutant allele in a sample of, for example, CTCs then comprises the steps of:
performing an asymmetric and allele specific Polymerase Chain Reaction (PCR), and performing a melting analysis of the DNA produced in the PCR, The PCR is carried out by the use of:
a mutant allele specific primer that is complementary to the 3' (three prime) end of a first strand of the mutant allele DNA target to be amplified,
an unlabeled blocking probe that is an oligonucleotide complementary to the wild type sequence of the first strand of wild type DNA corresponding to the first strand of the mutant allele and at the corresponding position in which the mutation to be detected is present, and which probe is blocked from acting as a primer for DNA synthesis in the PCR reaction; and
a common primer that is complementary to the 3' end of the second strand of the DNA target to be amplified by the PCR, The melting analysis is carried out by the use of
a melting probe being a non-labeled probe that is an oligonucleotide that comprises a sequence that is complementary to a wild type allele sequence and overlaps with a sequence of the mutant allele; and
a detectable component for measuring the melting temperature of double-stranded DNA components at least including the double-stranded component of the melting probe bound to an amplified mutant allele strand or wild allele strand, wherein the melting temperature differs between the double-stranded component of the melting probe bound to the amplified mutant allele strand and the melting probe bound to the amplified wild allele strand.

Allele specific PCR is then used to enrich rare alleles. The allele specific PCR requires a first primer being the mutant allele specific primer (reverse or forward) that is designed to be completely specific for the desired mutated allele and its 3'-end is designed to be exactly at the mutation site that should be detected. A second primer being the common primer (forward or reverse) is also used, which primer binds to the complementary strand that the first primer binds to and can be used for amplifying both the mutant and the wild type strand allele. In this way, the other alleles present in a sample, e.g. the wild type, are mismatched and non-specific amplification is limited. However by only using a mutant allele specific primer, this inhibition is not 100% complete in all cases described so far, since the wild type is usually present at an excess concentration.

Therefore, the method comprises the use of competitive probe blocking, wherein an unlabeled blocking probe is used. The unlabeled blocking probe (competitive probe) is an oligonucleotide complementary to the wild type sequence exactly in the position that the mutation to be detected is present. This unlabeled blocking probe is blocked at its 3'-end for use as a primer in the PCR, e.g. blocked by having an additional phosphate group at its 3'-end as compared to normal primers for PCR. This unlabeled blocking probe is used for competitive blocking of the wild type allele and is added at a higher concentration than the mutant allele specific primer, e.g. 5 to 20 times or 10 times higher concentration of the allele specific primer. There is an overlap in the sequences of mutant allele specific primer and the unlabeled blocking probe, and when both the mutant allele specific primer and this unlabeled blocking primer are present (wild type and mutant); the unlabeled blocking probe hybridizes to the wild type, and the mutant allele specific primer to the mutant allele. Thus, the unlabeled blocking probe competes with the allele specific primer for increased sensitivity, since it is designed to be matched with wild-type and thus binds exactly on the wild type allele. The unlabeled blocking probe may be designed so that corresponding hotspot mutations are placed as close to the center of the unlabeled blocking probe as possible. In this way, non-specific amplification of the wild type may be reduced to a minimum extent. Rare allele enrichment is optimal with an excess of blocking probe and reverse primer as compared with the allele specific primer.

The asymmetric PCR includes the allele specific PCR, wherein the mutant allele specific primer is added at a lower concentration (e.g. 10 times lower) in respect to a common primer. In this way this mutant allele specific primer is fully used in the PCR only by the mutant allele that is present at very low concentrations. In the presence of a mutant allele and after some PCR cycles the mutant allele specific primer is fully used, and the strand that includes the mutation information is then produced in an excess, since it is used as a constant template for the other primer that is common for both alleles and the amplification of the wild type allele is limited by the use of the mutant allele specific primer and the unlabeled blocking probe. The produced single-stranded PCR products contain the mutation information. After PCR, these are in excess and are recognized by the probe that is in excess, not completely complementary, so the melting curve is at a lower temperature.

The melting analysis follows the PCR reaction and includes a step of increasing the temperature from a temperature that is lower than the melting temperature of interest to a temperature above the melting temperature of interest and detecting the melting temperature of double-stranded DNA.

The melting analysis includes the use of a melting probe being a non-labeled probe that is an oligonucleotide that comprises a sequence that is complementary to a wild type allele sequence and overlaps with a sequence of the mutant allele, preferably around the position of the mutation. The melting probe (unlabeled blocking probe) may then comprise a sequence that overlaps with the sequence of mutant allele specific primer. The melting probe provides a different melting temperature for its binding to the mutant allele as compared to its binding to the wild type allele. The melting probe may, as also exemplified herein, be the unlabeled blocking probe. The melting temperature of the unlabeled blocking probe to the mutant allele is lower than the melting temperature of the unlabeled blocking probe to the wild type allele. The unlabeled blocking probe is added at a very high concentration, and this is mainly used in the reaction to block the wild type sequence, wherein the mutant allele specific primer will not be able to bind non-specifically to the wild type and give non-specific PCR products. Moreover, this same unlabeled blocking probe is recognizing the single strands that contain the mutation information as well as the wild type single strands as described above. As a result, the resulting melting curves are like signatures specific for the allele under the probe.

The measurement of the melting temperature between the melting probe and the complementary first strand of the asymmetric PGR product may be performed by the use of a fluorescence detection technique, wherein a fluorescent dye is used. In one embodiment, the fluorescent dye is a dye that emits fluorescence only in the presence of double stranded DNA in the measured sample. The dye may be LC-Green Plus. By measuring emission of fluorescence of double stranded DNA and the fluorescent dye LC-Green Plus, the melting curves are derived, that are characteristics for the mutant allele, since the melting temperature of the mutant DNA sequence is lower than that of the wild type sequence. The method may include increasing the temperature after the end of PCR reaction; when all the products are double stranded and emit fluorescence at 100%. Then the temperature is gradually increased, and fluorescence starts to decrease when the temperature reaches the one that is characteristic of the DNA sequence, that is the Tm. Tm is the temperature at which 50% of the DNA is double stranded and 50% is single stranded.

The melting analysis using the dye may, for example, comprise the steps of 55 to 60 degrees C. annealing for 10 s and 95 degrees C. for 1 min, wherein the temperature gradually is increased by 0.2 degrees C./s increments (ramp rate) beginning at the temperature of 55 to 60 degrees C. and measuring the melting temperature by detecting the dye (data collection step).

The mutant allele DNA target to be amplified in the PCR reaction may comprise or consist of exon 9 (SEQ NO ID: 1) and/or exon 20 (SEQ ID NO: 2) of PIK3CA and the mutant allele specific primer sequence is complementary to a DNA strand of the exon 9 (SEQ NO ID: 1) or exon 20 (SEQ NO ID: 2).

The melting probe may be the unlabeled blocking probe. The unlabeled blocking probe may have a 3'-end that is modified by an added phosphate group as compared to a PCR primer for amplification. This will block the use of the unlabeled blocking probe as a PCR primer for synthesis of a DNA strand. Optionally, the unlabeled blocking probe may be modified with one or more non-fluorescent moieties, such as but not limited to non-fluorescent minor-groove binders, biotin, spacers, linkers, phosphates, base analogs, nonnatural bases, and the like.

As discussed above, the detectable component may comprise a fluorescent component and wherein the melting analysis then may include detecting the fluorescent component. The fluorescent component may be a fluorescent dye, such as a fluorescent dye of the group that consists of LC-Green Plus or SYBR Green I that is emitting fluorescence only in the presence of double stranded DNA in the sample.

The unlabeled blocking probe is added at higher concentration than the mutant allele specific primer in the reaction in order to block the amplification of the wild type allele sequence. The unlabeled probe preferentially binds to the wild type DNA and competes with primer binding. At the same time, the lower concentration of the mutant allele specific primer leads to extend the mutant allele sequence only. Thus, the concentration of blocking probe should be higher than the mutant primer as to be bound to the excess of the wild type alleles. Moreover, the different concentrations between the mutant allele specific primer and the common primer lead to produce the strand that includes the mutation information in an excess in order to increase the sensitivity of the method.

The mutation may be present in Exon 9 (SEQ NO ID: 1) of PIK3CA, wherein the mutant allele specific primer comprises or consists of the sequence 5'-TTTCTCCTGATT-3' (SEQ ID NO: 3), wherein T indicates the mutation site and A indicates an additional mismatch which inhibits the amplification of the wild type allele sequence, in order to increase the amplification of the mutant rare alleles only and lead to enhance the specificity of method. The sequence of the mutant allele specific primer may preferably comprise or be 5'-ACTCCATAGAAAATCTTTCTCCTGATT-3' (SEQ ID NO: 4).

The unlabeled blocking probe may comprise or consist of the sequence 5'-CTGATCAGTGA-3' (SEQ ID NO: 5), wherein C indicates the exact position where the sequence is complementary to wild type site, and a PCR blocking component, which blocks the unlabeled blocking probe from acting as a primer for DNA synthesis in the PCR reaction.

The sequence of the unlabeled blocking probe may preferably comprise or be 5'-CTTTCTCCTGATCAGTGAT-TTCAGAG-P-3' (SEQ ID NO: 6), wherein P is phosphate acting as the PCR blocking component.

The common primer may have 75% to 100% identity to the sequence 5'-GCTCAAAGCAATTTCTACACGAGA-3' (SEQ ID NO: 7). This means that a common primer may have at least 75%, or at least 80%, or at least 85% or at least 90% identity, such as 75-100%, 76-100%, 77-100%, 78-100%, 79-100%, 80-100%, 81-100%, 82-100%, 83-100%, 84-100%, 85-100%, 86-100%, 87-100%, 89-100%, 90-100%, 91-100%, 92100%, 93-100%, 94-100%, 95-100%, 96-100%, 97-100%, 98-100%, 99-100% or about 100% identity, to the nucleic acid sequence 5'-GCTCAAAGCAATTTCTACACGAGA-3' (SEQ ID NO: 7).

The mutation may also be present in Exon 20 (SEQ ID NO: 2) of PIK3CA, wherein the mutant allele specific primer comprises or consists of the sequence 5'-AAT-GATGCACG-3' (SEQ ID NO: 8), 5'-GAATGATGCTCG-3' (SEQ ID NO: 16), or 5'-GAATGATGCTCT-3' (SEQ ID NO: 17), wherein G indicates the mutation site. The sequence of the mutant allele specific primer may preferably comprise or be 5'-ATGAAACAAATGAATGATGCACG-3' (SEQ ID NO: 9), 5'-ATGAAACAAATGAATGATGCTCG-3' (SEQ ID NO: 13) or 5'-: ATGAAACAAATGAATGATGCTCT-3' (SEQ ID NO: 14).

The unlabeled blocking probe may comprise or consist of a sequence 5'-TGCACATCATG-3' (SEQ ID NO: 10), wherein A indicates the exact position where the sequence is complementary to wild type site, and a PCR blocking component, which blocks the unlabeled blocking probe from acting as a primer for DNA synthesis in the PCR reaction. The sequence of the unlabeled blocking probe may preferably comprise or be 5'-GAATGATGCACATCATGGTGG-P-3' (SEQ ID NO: 11) or 5'-AATGAATGATGCTCAT-CATGGTG-P-3' (SEQ ID NO: 15), wherein P is phosphate acting as the PCR blocking component.

The common primer may then have 75% to 100% identity to the sequence 5'-TCTCAGTTATCTTTTCAGTT-CAATGC-3' (SEQ ID NO: 12). This means that a common primer may have at least 75%, or at least 80%, or at least 85% or at least 90% identity, such as 75-100%, 76-100%, 77-100%, 78-100%, 79-100%, 80-100%, 81-100%, 82-100%, 83-100%, 84-100%, 85-100%, 86-100%, 87-100%, 89-100%, 90-100%, 91100%, 92-100%, 93-100%, 94-100%, 95-100%, 96-100%, 97-100%, 98-100%, 99-100% or about 100% identity, to the nucleic acid sequence 5'-TCTCAGTTATCTTTTCAGTTCAATGC-3' (SEQ ID NO: 12).

The present document also relates to a method for
i) diagnosing malignant neoplastic disease in a subject, and/or
ii) predicting efficacy of treatment of malignant neoplastic disease in a subject, and/or
iii) assessing outcome of treatment of malignant neoplastic disease in a subject, and/or
iv) assessing recurrence of malignant neoplastic disease in a subject
wherein the subject is a mammal having, or is suspected of having, a malignant neoplastic disease,
wherein said method comprises analyzing presence of a PIK3CA mutant allele DNA in a sample according to the steps as described herein.

The method as described herein may advantageously be used for detecting a presence of a PIK3CA mutant allele DNA in a sample and i) diagnosing malignant neoplastic disease in a subject, and/or
ii) predicting efficacy of treatment of malignant neoplastic disease in a subject, and/or
iii) assessing outcome of treatment of malignant neoplastic disease in a subject, and/or
iv) assessing recurrence of malignant neoplastic disease in a subject
wherein the subject is a mammal having, or is suspected of having, a malignant neoplastic disease.

The sample analyzed may be a biological sample, and said biological sample may be obtained from a subject. Advantageously the subject is a human.

The malignant neoplastic disease may be selected from the group consisting of breast, colon, endometrial, esophageal, gastric, head and neck, liver, ovarian, thyroid, skin, pancreatic, prostate and stomach cancer.

Advantageously, the malignant neoplastic disease is breast cancer.

When diagnosing and/or prognosing malignant neoplastic disease in a subject, the method comprises the steps of
a) obtaining a biological sample from a given subject
b) performing the method for analyzing presence of a PIK3CA mutant allele DNA in a DNA sample obtained from said biological sample as described herein
c) detecting a presence of PIK3CA mutant allele DNA in said DNA sample; and
d) comparing the amount PIK3CA mutant allele DNA detected in said DNA sample to a positive and/or negative control, thereby diagnosing and/or prognosing the malignant neoplastic disease in the subject.

Further embodiments are wherein the positive control comprises cells from a cell line carrying the mutation. Even further embodiments are wherein the negative control comprises cells from healthy subjects who are not suffering from malignant neoplastic disease.

When predicting outcome of treatment in a subject suffering from malignant neoplastic disease or predicting response to treatment, the method comprises the steps of
a) obtaining a biological sample from a given subject
b) performing the method for analyzing the presence of a PIK3CA mutant allele DNA in a DNA sample obtained from said biological sample as described herein; and
c) detecting a presence of PIK3CA mutant allele DNA in said DNA sample; and
d) comparing the amount of PIK3CA mutant allele DNA detected in said DNA sample to a positive and/or negative control, thereby predicting the outcome of treatment of the malignant neoplastic disease in said subject based on the detected presence of PIK3CA mutant allele DNA in said DNA sample.

When assessing efficacy of treatment of malignant neoplastic disease in a subject who is being treated for malignant neoplastic disease, the method comprises the steps of
a) obtaining a biological sample from a subject who is undergoing treatment for malignant neoplastic disease
b) performing the method for analyzing the presence of a PIK3CA mutant allele DNA in a DNA sample obtained from said biological sample as described herein;
c) detecting a presence of PIK3CA mutant allele DNA in said DNA sample; and
d) repeating steps a) to c) at one or more time points during treatment of said subject for malignant neoplastic disease, and wherein a change in relative presence of PIK3CA mutant allele DNA in said DNA sample over time indicates the efficacy of treatment.

Thus, an indication of effective treatment is a relative change in decreasing presence of PIK3CA mutant allele DNA in said DNA sample relative a previous sample analyzed in the steps of repeating the method.

Optionally, a scoring may be done of the detected PIK3CA mutant allele DNA in said DNA sample according to a standard scoring system known in the art or described herein.

The sample may be any sample possibly comprising malignant neoplastic disease, preferably a biological sample from a subject having malignant neoplastic disease, and that subject will be, is in-between or is currently under treatment.

When assessing recurrence of malignant neoplastic disease, the method comprises the steps of
 a) obtaining a biological sample from a subject having previously had malignant neoplastic disease,
 b) detecting the presence of PIK3CA mutant allele DNA in a DNA sample obtained from said biological sample,
 c) repeating steps a) and b) at one or more time points post treatment of said subject for malignant neoplastic disease, and wherein a change in relative presence of PIK3CA mutant allele DNA in said DNA sample over time may indicate recurrence of malignant neoplastic disease.

Thus, an indication of recurrence is a relative change in increasing amounts of PIK3CA mutant allele DNA in said DNA sample that identify malignant neoplastic disease, i.e. an over-time increase in presence of PIK3CA mutant allele DNA in said DNA sample relative a previous sample analyzed in the steps of repeating the method.

The invention also relates to a polynucleotide for detecting presence of a mutation in exon 9 of PIK3CA in a sample, comprising or consisting of at least the sequence 5'-TTTCTCCTGATT-3' (SEQ ID NO: 3), preferably a sequence comprising or consisting of 5'-ACTCCATAGAAAATCTTTCTCCTGATT-3' (SEQ ID NO: 4), wherein T indicates a mutation site and A indicates an additional mismatch The polynucleotide may advantageously be used as the mutant allele specific primer for detecting the presence of a mutation in exon 9 of PIK3CA in the method as described above. The polynucleotide may be used as a prognostic marker for breast cancer.

The invention also relates to a polynucleotide for detecting presence of a mutation in exon 20 of PIK3CA in a sample, comprising or consisting of at least the sequence 5'-AATGATGCACG-3' (SEQ ID NO: 8), 5'-GAAT-GATGCTCG-3' (SEQ ID NO: 16), or 5'-GAAT-GATGCTCT-3' (SEQ ID NO: 17), preferably a sequence comprising or consisting of 5'-ATGAAACAAATGAAT-GATGCACG-3' (SEQ ID NO: 9), 5'-ATGAAACAAAT-GAATGATGCTCG-3' (SEQ ID NO: 13) or 5'-: ATGAAACAAATGAATGATGCTCT-3' (SEQ ID NO: 14), wherein G indicates the mutation site. The polynucleotide may be used as the mutant allele specific primer for detecting the presence of a mutation in exon 20 of PIK3CA in the method as described herein. The polynucleotide may be used as a prognostic marker for breast cancer.

The invention also relates to a kit for detecting a PIK3CA mutant allele DNA in a sample, like CTCs, ctDNA or FFPEs. The kit for detecting a mutation in PIK3CA in a sample may also be used for
 i) detecting a PIK3CA mutant allele DNA in a biological sample, and/or
 ii) detecting malignant neoplastic disease in a subject; or
 iii) diagnosing or prognosing malignant neoplastic disease in a subject; or
 iv) predicting outcome of treatment of malignant neoplastic disease in a subject; or
 v) assessing efficacy of treatment of malignant neoplastic disease in a subject; or
 vi) assessing recurrence of malignant neoplastic disease in a subject;

The kit may comprise
a first polynucleotide for detecting a mutation in exon 9 of PIK3CA in a sample, said first polynucleotide comprising or consisting of at least the sequence 5'-TTTCTCCTGATT-3' (SEQ ID NO: 3), preferably said first polynucleotide comprising or consisting of 5'-ACTCCATAGAAAATCTTTCTCCTGATT-3' (SEQ ID NO: 4), and/or
a second polynucleotide for detecting a mutation in exon 20 of PIK3CA in a sample, said second polynucleotide comprising or consisting of at least the sequence 5'-AATGATGCACG-3' (SEQ ID NO: 8), 5'-GAAT-GATGCTCG-3' (SEQ ID NO: 16), or 5'-GAAT-GATGCTCT-3' (SEQ ID NO: 17), preferably said second polynucleotide comprising or consisting of 5'-ATGAAACAAATGAATGATGCACG-3' (SEQ ID NO: 9), 5'-ATGAAACAAATGAATGATGCTCG-3' (SEQ ID NO: 13) or 5'-: ATGAAACAAATGAAT-GATGCTCT-3' (SEQ ID NO: 14). The first and/or second polynucleotides may be used as mutant allele specific primers in the method as described above.

The kit may further comprise a third polynucleotide comprising or consisting of at least the sequence 5'-CT-GATCAGTGA-3' (SEQ ID NO: 5) and a PCR blocking component, preferably said third polynucleotide comprises or is 5'-CTTTCTCCTGATCAGTGATTTCAGAG-P-3' (SEQ ID NO: 6), wherein P is phosphate and A an additional mismatch, and/or a fourth polynucleotide comprising or consisting of at least the sequence 5'-TGCACATCATG-3' (SEQ ID NO: 10) and a PCR blocking component, preferably wherein said fourth polynucleotide comprises or is 5'-GAATGATGCACATCATGGTGG-P-3' (SEQ ID NO: 11) or 5'-AATGAATGATGCTCATCATGGTG-P-3' (SEQ ID NO: 15), wherein P is phosphate. The third and/or fourth polynucleotides may be used as unlabeled blocking probes in the method described above.

The kit may further comprise a fifth polynucleotide having a sequence having 75% to 100% identity to the sequence 5'-GCTCAAAGCAATTTCTACACGAGA-3' (SEQ ID NO: 7), and/or a sixth polynucleotide having 75% to 100% identity to the sequence 5'-TCTCAGTTATCTTTTCAGTT-CAATGC-3' (SEQ ID NO: 12). The fifth and/or sixth polynucleotides may be used as common primers in the method described above.

BRIEF DESCRIPTION OF FIGURES

FIG. 7 presents the nucleotide sequences for exons 9 and 20.

DEFINITIONS

Figure 1:
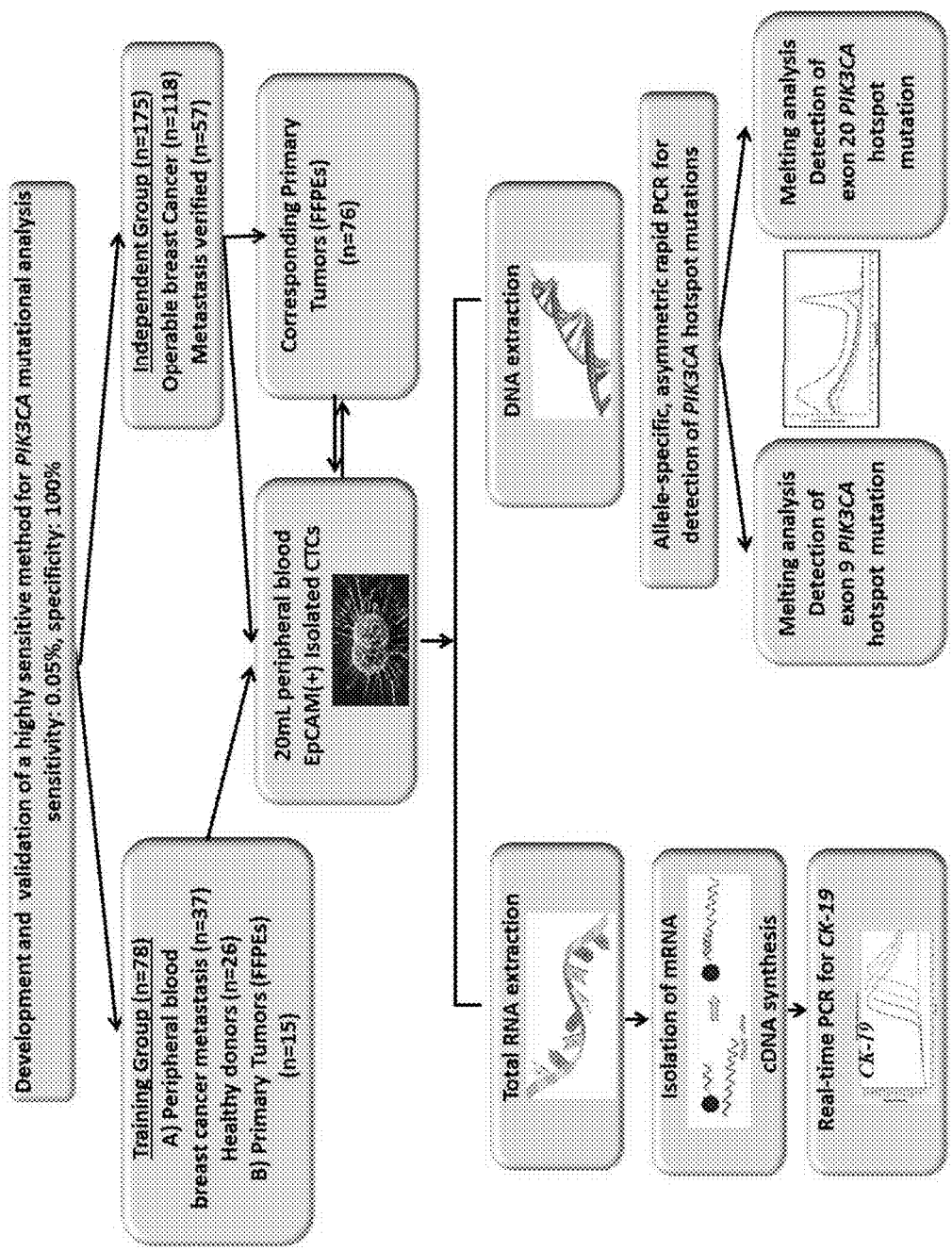
FIG. 1 illustrates the experimental flowchart of the current study.

The terms used in this invention are, in general, expected to adhere to standard definitions generally accepted by those having ordinary skill in the art of molecular biology. A few exceptions, as listed below, have been further defined within the scope of the present invention.

"At least one" as used herein means one or more, i.e., 1, 2, 3, 4, 5, 6, 7, 8, 9, 10 etc.

"Detection", "detect", "detecting" as used herein includes qualitative and/or quantitative detection (measuring levels) with or without reference to a control, and further refers to the identification of the presence, absence, or quantity of a given PIK3CA mutant allele DNA molecule.

As used herein, the term "nucleic acid sequence", "nucleic acid molecule", "nucleic acid" and the like refers to a polynucleotide molecule (DNA—deoxyribonucleic acid, or RNA—ribonucleic acid) comprising a string of nucleic acid bases. These nucleic acid bases are "A" (adenine), "T" (thymidine)/"U" (uracil), "C" (cytidine) and "G" (guanidine). In RNA, "T" is replaced with "U". DNA or RNA may be single-stranded or double-stranded. By an RNA sequence "corresponding to" a nucleic acid sequence expressed herein as a DNA sequence, the same nucleic acid sequence but wherein "T" is replaced by "U" to get the corresponding RNA sequence is intended. The term, "nucleic acid" may comprise both DNA and/or RNA sequences unless one or the other is specifically referred to.

As used herein in connection with nucleic acid molecules (DNA and RNA molecules), the term "isolated" means that the molecule has been removed from its original environment. This means that a nucleic acid molecule when present in a living organism is not "isolated". Breaking of chemical bonds and/or by other means separating the sequence from its natural environment means that the nucleic acid molecule is "isolated".

As used herein, the term "primer" refers to an oligonucleotide which, produced synthetically, is capable of acting as a point of initiation of nucleic acid synthesis when placed under conditions in which synthesis of a primer extension product which is complementary to a nucleic acid strand is induced, i.e., in the presence of nucleotides and an agent for polymerization such as DNA polymerase, reverse transcriptase or the like, and at a suitable temperature and pH. The primer is preferably single stranded for maximum efficiency, but may alternatively be double stranded. If double stranded, the primer is first treated to separate its strands before being used to prepare extension products. The primer must be sufficiently long to prime the synthesis of extension products in the presence of the agents for polymerization. The exact lengths of the primers will depend on many factors, including temperature and the source of primer. For example, depending on the complexity of the target sequence, a primer typically contains 15 to 25 or more nucleotides, although it can contain fewer nucleotides. Short primer molecules generally require cooler temperatures to form sufficiently stable hybrid complexes with a template.

The term "mutant allele-specific primer" refers to a primer that hybridizes to mutant allele sequence and is capable of discriminating between the variants of the target sequence in that only with the mutations, the primer is efficiently extended by the nucleic acid polymerase under suitable conditions. With other variants of the target sequence, the extension is less efficient or inefficient.

The term "forward primer" refers to a primer that forms an extension product by binding in the 5' to 3' direction to the 3' end of a strand of a denatured DNA analyte.

The term "reverse primer" refers to a primer that forms an extension product by binding in the 3' to 5' direction to the 5' end of a strand of a denatured DNA analyte.

The term "amplicon" refers to the amplification product of a nucleic acid extension assay, such as PCR.

The term "unlabeled probe" refers to an oligonucleotide that is not covalently linked to a dye and that is configured to hybridize perfectly or partially to a target sequence. The dye that is present in the mixture is free to bind to or disassociate from the unlabeled probe, particularly as the probe hybridizes to and melts from the target sequence.

The term blocking probe or competitive probe refers to an oligonucleotide that is complementary to a wild type allele sequence and competes with the mutant allele specific primer in order to avoid the amplification of non-specific wild type products.

As used herein, the term "melting temperature" (Tm) in relation to an oligonucleotide is defined as the temperature at which 50% of the DNA forms a stable double-helix and the other 50% has been separated into single stranded molecules. As known to those of skill in the art, PCR annealing temperature is typically a few degrees less than the Tm, the latter of which is calculated based on oligo and salt concentrations in the reaction.

The terms "complementary" or "complementarity" are used in reference to antiparallel strands of polynucleotides related by the Watson-Crick base-pairing rules. The terms "perfectly complementary" or "100% complementary" refer to complementary sequences that have Watson-Crick pairing of all the bases between the antiparallel strands, i.e., there are no mismatches between any two bases in the polynucleotide duplex. However, duplexes are formed between antiparallel strands even in the absence of perfect complementarity. The terms "partially complementary" or "incompletely complementary" refer to any alignment of bases between antiparallel polynucleotide strands that is less than 100% perfect (e.g., there exists at least one mismatch or unmatched base in the polynucleotide duplex). The duplexes between partially complementary strands are generally less stable than the duplexes between perfectly complementary strands.

The terms "polynucleotide" and "oligonucleotide" are used interchangeably. "Oligonucleotide" is a term sometimes used to describe a shorter polynucleotide.

The terms "hybridized" and "hybridization" refer to the base-pairing interactions between two nucleic acids that result in formation of a duplex. It is not a requirement that two nucleic acids have 100% complementarity over their full length to achieve hybridization.

By "variant thereof" or "variants thereof and the like, as used in the present document, a nucleic acid sequence(s) is intended, having an identity to a specified nucleic acid sequence of at least 85% or at least 90%, such as 85-100%, 86-100%, 87-100%, 89100%, 90-100%, 91-100%, 92-100%, 93-100%, 94-100%, 95-100%, 96-100%, 97-100%, 98-100%, 99-100% or about 100%.

PCR (polymerase chain reaction) is a method for amplification of nucleic acid molecules. The PCR reaction is well-known to the person skilled in the art and involves contacting a sample with a pair of so called oligonucleotide primers (one forward and one reverse primer) under conditions allowing the hybridization between the primers and a target (template) sequence having complementarity to the primers and which target sequence possibly is present in the sample in order to amplify the target sequence.

"Diagnosis" as used herein encompasses the identification of the nature of a disease.

"Prognosis" as used herein encompasses a forecast as to the probable outcome of a disease, the prospects as to recovery from a disease as indicated by the nature and symptoms of a disease.

"True positives" refers to the presence of PIK3CA specific mutations in a localized or a metastasized malignant neoplasm.

"False negatives" refers to the presence of PIK3CA specific mutations either in a localized or a metastasized malignant neoplasm and are not categorized as such by a diagnostic assay.

"True negatives" refers to those subjects who do not have a localized or a metastasized malignant neoplasm and who are categorized as such by a diagnostic assay.

"False positives" refers to those subjects who do not have a localized or a metastasized malignant neoplasm but are categorized by a conventional diagnostic assay as having a localized or metastasized malignant neoplasm.

Depending on context, the term "false positives" may also refer to those subjects who do not have malignant neoplasm but are categorized by a diagnostic assay as having malignant neoplasm or a non-malignant disease.

"Sensitivity", as used herein in the context of its application to diagnostic assays, refers to the proportion of all subjects with localized or metastasized malignant neoplasm that are correctly identified as such (that is, the number of true positives divided by the sum of the number of true positives and false negatives).

"Specificity" of a diagnostic assay, as used herein in the context of its application to diagnostic assays, refers to the proportion of all subjects with neither localized or metastasized malignant neoplasm that are correctly identified as such (that is, the number of true negatives divided by the sum of the number of true negatives and false positives).

The terms "neoplasm" or "tumor" may be used interchangeably and refer to an abnormal mass of tissue wherein the growth of the mass surpasses and is not coordinated with the growth of normal tissue. A neoplasm or tumor may be defined as "benign" or "malignant" depending on the following characteristics: degree of cellular differentiation including morphology and functionality, rate of growth, local invasion and metastasis. A "benign" neoplasm is generally well differentiated, has characteristically slower growth than a malignant neoplasm and remains localized to the site of origin. In addition a benign neoplasm does not have the capacity to infiltrate, invade or metastasize to distant sites.

A "malignant" neoplasm is generally poorly differentiated (anaplasia), has characteristically rapid growth accompanied by progressive infiltration, invasion, and destruction of the surrounding tissue. Furthermore, a malignant neoplasm has the capacity to metastasize to distant sites. The term "metastasis" refers to the spread or migration of cancerous cells from a primary (original) tumor to another organ or tissue, and is typically identifiable by the presence of a "secondary tumor" or "secondary cell mass" of the tissue type of the primary (original) tumor and not of that of the organ or tissue in which the secondary (metastatic) tumor is located. For example, a carcinoma of the lung that has migrated to bone is said to be metastasized lung cancer, and consists of cancer cells originating from epithelial lung cells growing in bone tissue.

"Healthy" refers to a subject possessing good health. Such a subject demonstrates an absence of any malignant or non-malignant disease. In the context of this application, a "healthy individual" is only healthy in that they have an absence of any malignant or non-malignant disease; a "healthy individual" may have other diseases or conditions that would normally not be considered "healthy".

"Subject" as used herein includes humans, nonhuman primates such as chimpanzees and other apes and monkey species, farm animals such as cattle, sheep, pigs, goats and horses, domestic mammals such as dogs and cats, laboratory animals including rodents such as mice, rats and guinea pigs, and the like. The term does not denote a particular age or sex. Thus, adult and newborn subjects, as well as fetuses, whether male or female, are intended to be covered. In preferred embodiments, the subject is a mammal, including humans and non-human mammals. In the most preferred embodiment, the subject is a human.

"Blood plasma" or "plasma" is the straw-colored/pale-yellow liquid component of blood that normally holds the blood cells in whole blood in suspension. It makes up about 55% of total blood by volume. It is the intravascular fluid part of extracellular fluid (all body fluid outside of cells). It is mostly water (93% by volume), and contains dissolved proteins including albumins, immunoglobulins, and fibrinogen, glucose, clotting factors, electrolytes ($Na^+$, $Ca^{2+}$, $Me^{2+}$, $HCO^{3-}$, $Cl^-$ etc.), hormones and carbon dioxide.

As used herein a "biological sample" encompasses a variety of sample types obtained from any subject having or not having malignant neoplasm. A typical subject is a human. For example, biological samples include samples obtained from a tissue or blood fluids collected from an individual suspected of having a malignant neoplasm.

The term "treatment" as used herein is defined as the management of a patient through medical or surgical means. The treatment improves or alleviates at least one symptom of a medical condition or disease and is required to provide a cure. The term "treatment outcome" or "outcome of treatment" as used herein is the physical effect upon the patient of the treatment.

As used herein the term circulating tumor cells (CTC) are cells that have shed into the vasculature from a primary tumor and circulate in the bloodstream. CTCs thus constitute seeds for subsequent growth of additional tumors (metastasis) in vital distant organs, triggering a mechanism that is responsible for the vast majority of cancer-related deaths The term, cell-free DNA (cfDNA) refers to DNA that is released to the circulation from cells undergoing apoptosis or other physiological events induced by micro-environmental stress. The cfDNA can be detected in the blood of patients with cancer.

The term circulating tumor DNA (ctDNA) refers to DNA that is released to the circulation from cells of the primary tumor and provide information about the status of the primary tumor or metastatic tumor.

As used herein, the term PIK3CA refers to the official name of the gene called "phosphatidylinositol-4,5-bisphosphate 3-kinase, catalytic subunit alpha.". The phosphatidylinositol 3-kinase (PI3K)/AKT signaling pathway is implicated in human diseases including cancer, and understanding the intricacies of this pathway may provide new avenues for therapeutic intervention. Somatic mutations in the p110a catalytic subunit of PI3K, are very frequent and play a crucial role in response to molecular target therapies and often co-occur with HER-2 amplification in breast cancer. The mutations of PIK3CA have been reported in 18%-40% of breast cancer patients, while the vast majority, comprising approximately 90% of cases, are clustered at two hot-spot regions in exon 9 and exon 20, which encode the helical and kinase domains, respectively. Aberrant activation of the PI3K pathway correlates with a diminished response to HER2-directed therapies, as the outcome of HER2-positive patients treated with trastuzumab is significantly worse in patients with PIK3CA-mutated compared with wild-type tumors.

The term mutant allele DNA refers to the DNA sequence that includes at least one mutation between two exons in PIK3CA gene according to the reference sequence. The mutant allele DNA could have either the 1633G>A hotspot mutation in exon 9 or the 3140A>G hotspot mutation in exon 20.

The mutation is a permanent alteration in the DNA sequence that makes up a gene, such that the sequence differs from what is found in reference sequence. Mutations range in size; they can affect anywhere from a single DNA building block (base pair) to a large segment of a chromosome that includes multiple genes.

As used herein, the term "reference genome" or "reference sequence" refers to any particular known genome sequence, whether partial or complete, of any organism or virus which may be used to reference identified sequences from a subject. For example, a reference genome used for human subjects as well as many other organisms is found at the National Center for Biotechnology Information at www.ncbi.nlm.nih.gov. A "genome" refers to the complete genetic information of an organism or virus, expressed in nucleic acid sequences.

The term "wild allele strand" refers to the DNA sequence that encodes the phenotype most common in a particular natural population. Originally, the wild type was conceptualized as a product of the standard "normal" allele at a locus, in contrast to that produced by a non-standard, "mutant" allele.

The term "hotspot mutation" refers to mutations occurring at a chromosomal region, which is more susceptible to genetic damage/change than average sequences.

DETAILED DESCRIPTION

The present invention provides an ultra-sensitive and highly specific molecular method for high throughput mutation detection of PIK3CA hotspots mutations in a sample of, for example, circulating tumor cells or circulating tumor DNA. The importance of PIK3CA mutations is associated with the response to molecular targeted therapies in breast cancer.

MATERIALS AND METHODS

Patients
As a training group, a total of 78 samples were analyzed: i) 63 peripheral blood samples; 37 from patients with clinically confirmed metastasis and 26 from healthy female volunteers, used to define the specificity of the assay, and ii) 15 primary breast tumor tissues (FFPEs). As an independent group, a total of 175 peripheral blood samples were obtained from 118 patients with operable breast cancer and 57 patients with clinically confirmed metastasis; in addition, for 76 of these breast cancer patients (32 with metastasis and 44 with operable breast cancer) FFPEs from the primary tumor were also analyzed. For 157 of these samples, information on the expression of CK-19 in the EpCAM positive CTC fraction was also available through previous studies. In the independent group of the 118 patients with operable breast cancer 9 patients relapsed and died due to disease progression (median follow up: 42 months). In addition, patients with HER2+tumors received trastuzumab for 12 months whereas patients with HR+tumors received endocrine treatment (either LH/RH analogues plus tamoxifen or aromatase inhibitors). Adjuvant radiotherapy was also administered according to the guidelines. All study participants signed an informed consent form to participate in the study, which was approved by the ethics and scientific committees of the institutions.

Positive Immunomagnetic Selection of CTC
CTC were isolated from 20 mL peripheral blood as previously described [Strati A, et al. Gene expression profile of circulating tumor cells in breast cancer by RT-qPCR. BMC Cancer 2011; 11:422]. More specifically, after dilution of peripheral blood with 20 mL PBS (pH=7.3), peripheral blood mononuclear cells (PBMC) were obtained by gradient density centrifugation using Ficoll-Paque TM PLUS (GE Healthcare, Bio-Science AB) at 670 g for 30 min at room temperature. The interface cells were removed, washed twice with 40 mL of sterile PBS (pH=7.3, 4° C.) at 530 g for 10 min, and resuspended in 10 mL of PBS. Cells were dyed with trypan blue and counted in a hemocytometer. Immunomagnetic Ber-EP4 [anti-epithelial cell adhesion molecule (EpCAM)]-coated capture beads (Dynabeads Epithelial Enrich, Invitrogen) were used to enrich for epithelial cells.

DNA Extraction from CTC
Genome DNA (gDNA) was extracted from CTC as previously described [Chimonidou M, et al. DNA methylation of tumor suppressor and metastasis suppressor genes in circulating tumor cells. Clin Chem 2011; 57:1169-77]. After removal of the aqueous phase of Trizol, DNA was precipitated (from the interphase) by adding 150 µL of 100% ethanol. Samples were mixed by inversion and kept at room temperature for 2-3 min, and then DNA was sedimented by centrifugation (2000 g, 5 min, 4° C.) and washed twice in a solution containing 0.1 mol/L sodium citrate in 10% ethanol (500 µL). After each wash, the DNA pellet was stored in the washing solution for 30 min at room temperature with periodic mixing and centrifuged (2000 g, 5 min, 4° C.). Following these 2 washes, the DNA pellet was suspended in 1 mL of 75% ethanol, kept for 10-20 min at room temperature with periodic mixing and centrifuged (2000 g, 5 min, 4° C.). Isolated gDNA was then air dried for 15 min and dissolved in 50 µL of 8 mmol/L NaOH. The DNA concentration was determined in the Nanodrop ND-1000 spectrophotometer. Peripheral blood from 26 female healthy volunteers that was collected for specificity studies was processed by using exactly the same procedure as used for patients' samples.

DNA Extraction from Plasma
Cell-free DNA was isolated from plasma samples using the QIAamp Circulating Nucleic Acid kit (QIAGEN) according to the manufacturer's instructions. Firstly, peripheral blood samples in EDTA were within 1 hour used for isolation in plasma, and plasma samples were stored at −70° C. till cfDNA isolation. Just before cfDNA isolation, plasma samples were thawed at room temperature and centrifuged at 13,400 g for 10 min at 4° C. to remove residual precipitated cellular components. In all, 2.00 mL of plasma was mixed with 1.6 mL Buffer ACL (containing 1.0 µg carrier RNA) of working solution and 200 µl proteinase K (18 mg ml$^{-1}$) and incubated for 30 min at 60° C. DNA isolation was then processed as described in the manufacturer's protocol.

Primer and Probe Designs

All oligonucleotides were de novo in-silico designed for each of PIK3CA exon 9 (SEQ ID NO: 1) and exon 20 (SEQ ID NO: 2), by using the PrimerPremier 5 software (Premier Biosoft International), and synthesized by IDT (Intergraded DNA Technologies). The sequences for exon 9 (SEQ ID NO: 1) and exon 20 (SEQ ID NO: 2), see FIG. 7. For each exon, one allele-specific primer (matched to 1633 G>A mutation for exon 9 and to 3140 A>G mutation for exon 20), one unlabeled competitive blocking probe, and one primer for asymmetric amplification were designed according to the study of Zhou and colleagues [Zhou L, et al. Rare allele enrichment and detection by allele-specific PCR, competitive probe blocking, and melting analysis. BioTechniques 2011; 50:311-8]. For exon 9, primer set S1 was designed to amplify the region (70 bp) that includes the hotspot mutation of exon 9. Reverse primer (allele-specific primer) was designed to amplify the mutant allele by matching the 30 end to the derived allele. Unlabeled probe and forward primers were designed to be matched with wild-type. Blocking probe competes with the allele-specific primer for increased sensitivity. For exon 20, primer set S2 was designed to amplify the region (104 bp) that includes the hotspot mutation of exon 20. Forward primer (allele-specific primer) was designed to amplify the mutant allele by matching the 30 end to the derived allele. Unlabeled probe and reverse primers were designed to be matched with wild-type. Hotspot mutations were placed as close to the center of the unlabeled probe as possible. All primers and probes were designed with attention to avoiding amplification of a pseudogene on chromosome 22 that has >95% homology to exon 9 of PIK3CA. All primers and probes sequences are given in detail in Table 1.

TABLE 1

Sequences of primers and probes designed and used in this study

| Exon 9 (1633 G > A mutation) | |
|---|---|
| Reverse primer (mutant allele specific primer) | 5'-ACTCCATAGAAAATCTTTCCTGATT-3' (SEQ ID NO: 4), S1 |
| Forward primer (common primer) | 5'-GCTCAAAGCAATTTCTACACGAGA-3' (SEQ ID NO: 7), S1 |
| Unlabeled blocking probe | 5'-CTTTCTCCTGATCAGTGATTTCAGAG-P-3' (SEQ ID NO: 6), S1 |
| Exon 20 (3140 A > G mutation) | |
| Forward primer (mutant allele specific primer) | 5'-ATGAAACAAATGAATGATGCACG-3' (SEQ ID NO: 9), S2 |
| Reverse primer (common primer) | 5'-TCTCAGTTATCTTTTCAGTTCAATGC-3' (SEQ ID NO: 12), S2 |
| Unlabeled probe | 5'-GAATGATGCACATCATGGTGG-P-3' (SEQ ID NO: 11), S2 |

PCR and Melting Analysis

Real-time PCR and melting curves were obtained using the LightScanner 32 (Idaho Technology, USA) using glass capillary tubes (Roche Applied Science, Germany). However, the same results can be also obtained by using the LightCycler 2.0 (IVD) instrument and LightCycler 480 (Roche Diagnostics). The LC-Green Plus (Idaho Technology, USA) was used for fluorescence measurements. Two gDNA samples isolated from MCF-7 (c.1633G>A: E545K; heterozygous), and T47D (c.3140A>G:H1047R; heterozygous) breast cancer cell lines were used as PIK3CA mutant controls. PCR conditions and melting analysis protocols for each exon are described in detail in Table 2. The PCR reaction mix for each exon is described in detail in Table 3.

TABLE 2

PCR conditions and melting analysis
protocols for each PIK3CA exon

|  | Exon 9 (1633 G > A) | Exon 20 (3140 A > G) |
|---|---|---|
| PCR conditions 80 cycles | 95° C./2 min<br>95° C./0 s<br>61° C./4 s | 95° C./2 min<br>95° C./5 s<br>63° C./5 s<br>72° C./3 s |
| Melting curve Conditions | 60° C./10 s<br>95° C./1 min<br>405° C./1 min | 55° C./10 s<br>95° C./1 min<br>40° C./1 min |

TABLE 3

PCR reaction mix for the detection of PIK3CA hotspot mutations in exon 9 and exon 20

| | Exon 9 (1633 G > A mutation) | | | Exon 20 (3140 A > G mutation) | | |
|---|---|---|---|---|---|---|
| Reagents | Initial conc | V(µL) | Final conc | Initial conc | V(µL) | Final conc |
| Forward primer | 10 µM | 0.5 | 0.5 µM | 1 µM | 1.0 | 0.1 µM |
| Reverse primer | 1 µM | 0.5 | 0.05 µM | 10 µM | 1.0 | 1.0 µM |
| Unlabeled probe | 10 µM | 0.5 | 0.5 µM | 10 µM | 1.0 | 1.0 µM |
| dNTP's | 10 mM | 0.2 | 0.2 mM | 10 mM | 0.2 | 0.2 mM |
| MgCl$_2$ | 25 mM | 1.0 | 2.5 mM | 25 mM | 0.8 | 2.0 mM |
| BSA | 10 µg/µL | 0.5 | 0.5 µg/µL | 10 µg/µL | 0.5 | 0.5 µg/µL |
| PCR buffer | 5X | 2.0 | 1X | 5X | 2.0 | 1X |
| Taq polymerase | 5 U/µL | 0.1 | 0.05 U/µL | 5 U/µL | 0.1 | 0.05 U/µL |
| LC Green I | 10X | 1.0 | 1X | 10X | 1.0 | 1X |
| H$_2$O | — | 1.7 | — | — | 1.4 | — |
| gDNA | 25 ng/µL | 2.0 | 5.0 ng/µL | 50 ng/µL | 1.0 | 5.0 ng/µL |

Statistical Analysis

Correlations between PIK3CA mutational status in CTCs and primary tumors were assessed by using the Chi-square test. Cohen's kappa coefficient, a statistical measure of inter-rater agreement or inter-annotator agreement for qualitative items, was used for the evaluation of agreement between PIK3CA mutations in CTCs and primary tumors, as well as between PIK3CA mutations in CTCs and CK-19 mRNA expression since it is generally thought to be a more robust measure than simple percent agreement calculation since k takes into account the agreement occurring by chance. Disease Free Interval (DFI) and Overall Survival (OS) curves were calculated by using the Kaplan-Meier method and comparisons were performed using the log rank test P values <0.05 were considered statistically significant. Statistical analysis was performed using the SPSS Windows version 19.0 (SPSS, Chicago, IL).

EXAMPLE 1

Development and Validation of an Ultrasensitive and Highly Specific Method for PIK3CA Hotspot Mutations The experiment flowchart of the study is outlined in FIG. 1.

Initially, an ultrasensitive and highly specific methodology for PIK3CA hotspot mutations (exon 9 and 20) in CTC was developed and validated. This assay is performed in a closed tube format and is based on the combination of allele-specific priming, competitive probe blocking of wild-type amplification, asymmetric PCR, and probe melting analysis [Markou A, et al. PIK3CA mutational status in circulating tumor cells can change during disease recurrence or progression in patients with breast cancer. Clin Cancer Res. 2014 Nov. 15; 20(22):5823-34], In this assay design, allele-specific PCR sensitivity and specificity were enhanced with an unlabeled competitive wild-type specific blocking probe by asymmetric amplification and probe melting analysis. The melting analysis peak of this unlabeled competitive probe at 60° C. was able to indicate the presence of PIK3CA mutations in both exons. The peak of the derivative melting curve of the unlabeled blocking probe and the DNA template of the WT PIK3CA exon 9, as amplified with the WT allele-specific primer, and the peak of the melting curve of the unlabeled blocking probe and the DNA template of the mutant PIK3CA exon 9, as amplified with the mutant allele-specific primer differ around 4° C. in both cases (results not shown). In all experiments, targeting the mutant allele, the mutation is detected by the derivative melting of this unlabeled blocking probe and mutant PIK3CA sequence, as amplified with the mutant allele-specific primer. So, a mutation is only detected if this peak at this lower temperature 60° C. is present. The other peak that is due to the PCR product and can be detected at higher temperatures can be seen for both the mutant and WT, in case that there is a non-specific amplification of the WT, by using the mutant allele-specific primer. All primers and probes were de-novo in-silico designed for each of PIK3CA exons 9 and 20, with attention to avoiding amplification of a pseudogene on chromosome 22 that has >95% homology to exon 9 of PIK3CA.

Protocol optimization. The PIK3CA mutation assay was extensively optimized for both exons in a number of experiments, using as positive and negative controls gDNA samples from cancer cell lines (MCF-7 and T47D) and wild-type (WT) gDNA isolated from healthy donors, with respect to: PCR annealing temperature, Mg$^{+2}$ concentration, primer and unlabeled probe concentration, the number of PCR cycles, duration of each asymmetric PCR step, primer ratio for asymmetric PCR and amount of target DNA, and melting analysis conditions (data not shown).

To develop a highly specific method with a low detection limit for the detection of PIK3CA mutations in CTCs, the protocol and conditions were initially optimized according to the best results. Allele specific PCR amplification and detection were enhanced by using asymmetric PCR, a wild type blocking probe, and probe melting analysis. Rare allele enrichment was optimal with an excess of blocking probe and common primer compared with the allele specific primer. It was observed that as the concentration of the mutant allele specific primer decreased, the specificity increased while the PCR efficiency decreased. Increasing specificity was reflected by the ΔCq between wild type and PIK3CA DNA. Decreasing PCR efficiency was evidenced by an increase in the Cq of PIK3CA DNA. Although, PCR efficiency was affected by decreasing the concentrations of either primer, only lower concentrations of the mutant allele specific primer increased the specificity. In order to compensate for the lower PCR efficiency, 80 cycles were typically performed.

Allele specific enrichment with a blocking probe is affected by the annealing/extension temperature. Specificity is optimal when the annealing/extension temperature is between the melting temperatures (Tm) of the wild type blocking probe for the matched wild type allele and the mismatched mutation allele. If the annealing temperature is lower than or equal to the Tm of the mutant allele, the probe suppresses amplification of both wild type and mutant alleles, limiting the sensitivity. If the annealing temperature is higher than or equal to the Tm of the wild type allele, preferential blockage and PCR efficiency decrease limiting the sensitivity.

EXAMPLE 2

Figure 2A:
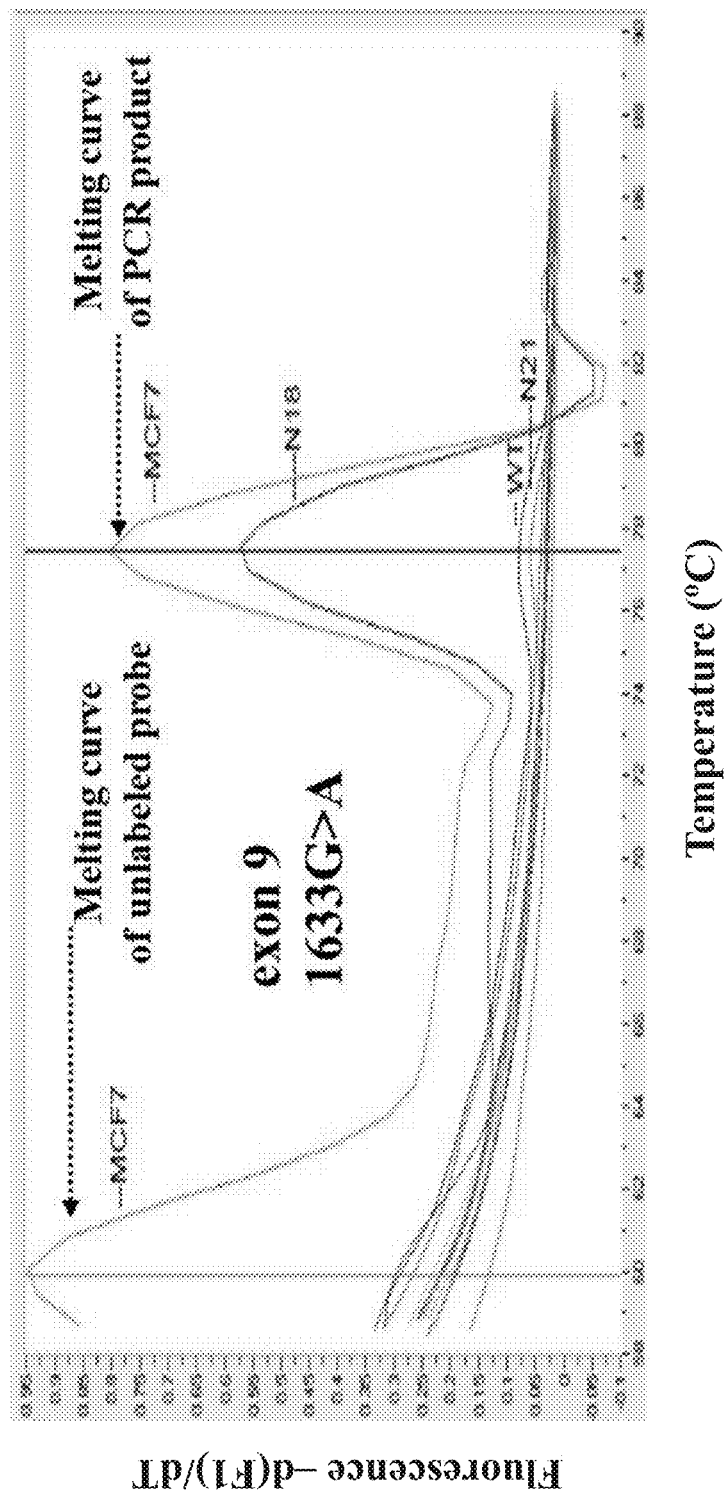
FIG. 2A-D depicts the specificity of the developed PIK3CA mutation assay for exon 9 1633 G>A (A) and for exon 20 3140 A>G (B) and the sensitivity of the developed PIK3CA mutation assay for exon 9 1633 G>A (C) and for exon 20 3140 A>G (D).
Figure 2B:
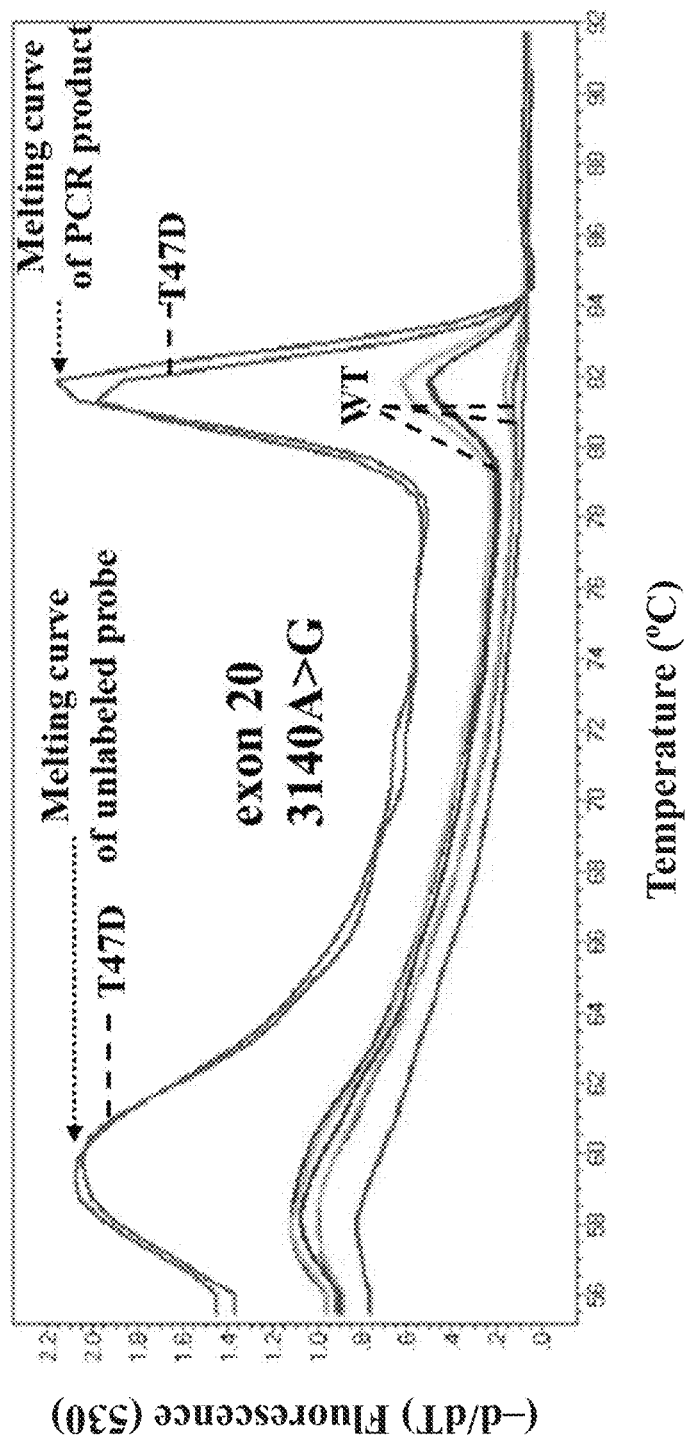

Specificity study. The assay specificity of the developed method was first evaluated by analyzing gDNA isolated from 26 healthy female volunteers, in exactly the same way that was followed for patients with breast cancer. The developed method is highly specific, since there was no case of healthy female donors with any mutation in both PIK3CA exons in any of these samples. FIGS. 2A and B depict the specificity of the developed PIK3CA mutation assay and characteristic derivative melting curves obtained after PCR in the presence of unlabeled blocking probes which detect exon 9 1633G>A, hotspot mutation (A) and exon 20 3140A>G, hotspot mutation (B) are shown. Baseline is PCR negative control. PIK3CA mutations are detected by the derivative melting of the unlabeled blocking probe and mutant PIK3CA sequence, as amplified with the mutant allele-specific primer. Mutations are detected only if this peak at 60° C. is present. The other peak at higher temperatures is due to the PCR product and can be seen for both the mutant and WT, in case that there is a nonspecific amplification of the WT, by using the mutant allele-specific primer.

As can be seen in FIG. 2a, in exon 9, one of the healthy donor's gDNA (N18) was amplified by the amplification-refractory mutation system (ARMS)-PCR-specific primer and gave a peak at 77.5° C., but not at 60.0° C. This could be explained by the fact that even by using the PIK3CA hotspot mutation-specific primers, a very low amount of the wild-type sequence that is present at very high concentrations could be nonspecifically amplified. To avoid this, the unlabeled probe that plays a key role as a blocker was used, as it is wild-type specific and binds at the same sequence as the mutant-specific primer. In the case of N18, this WT sequence was nonspecifically amplified and this is why the melting curve peak at 77.5° C. was detected. However, it isn't detected any peak at the melting curve for the unlabeled probe at 60.0° C. that is specifically indicating the presence of the specific mutation that we are looking for. These results confirm the 100% specificity of the method.

EXAMPLE 3

Figure 2C:
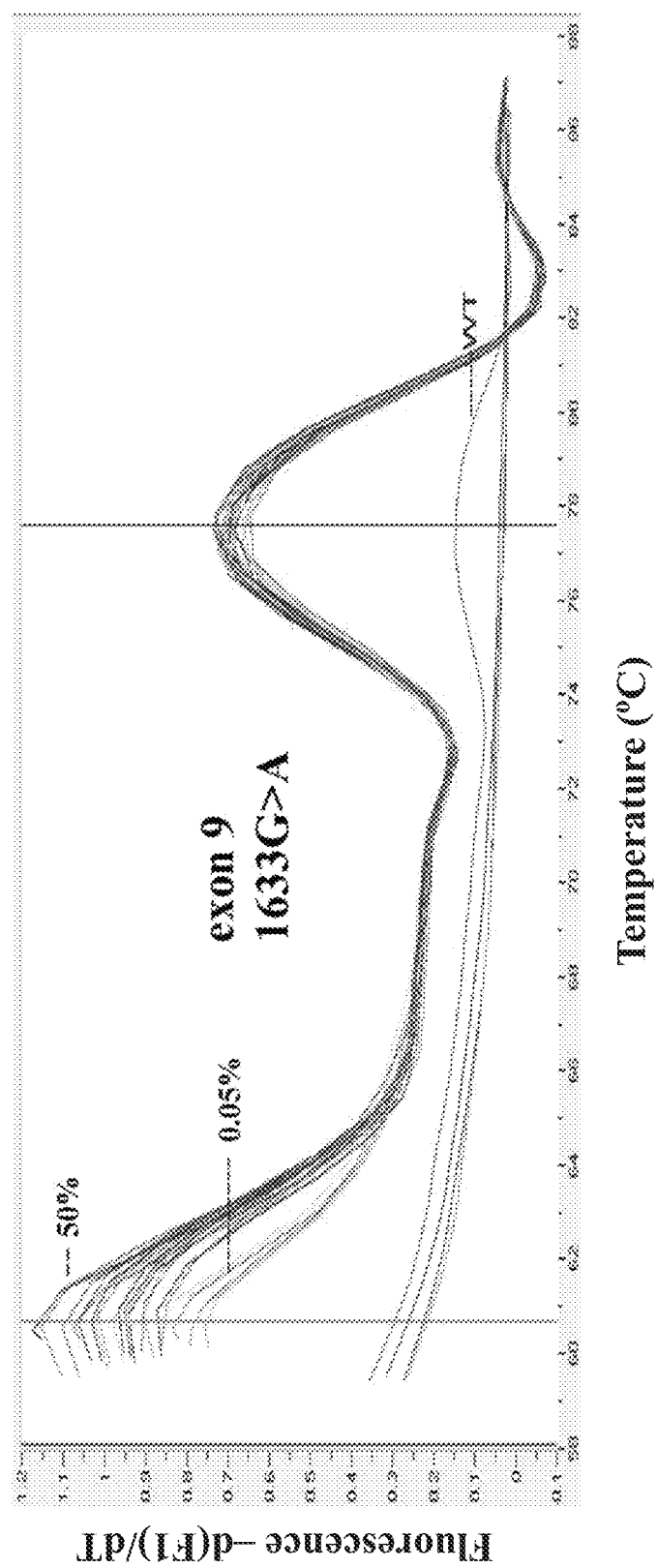
Figure 2D:
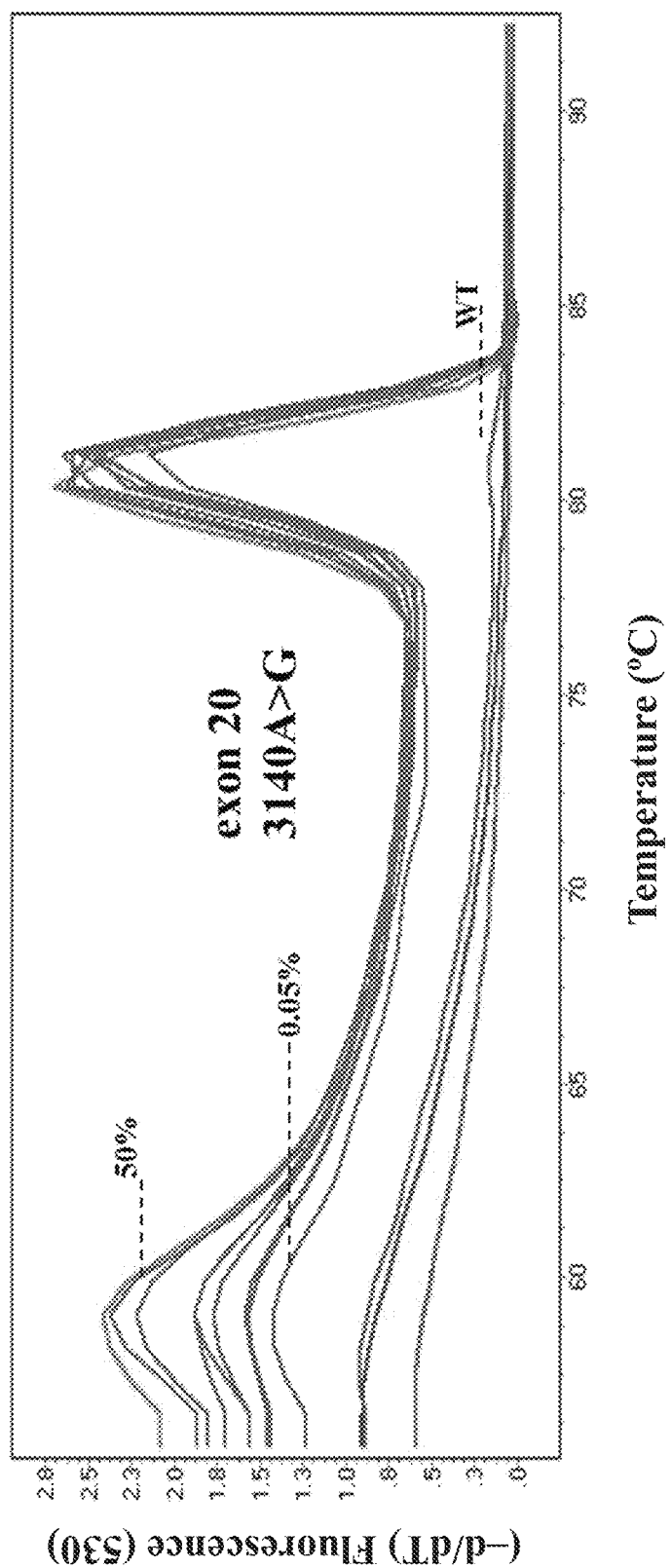

Sensitivity study. The sensitivity of the developed method was further evaluated by mixing mutated gDNA from cell lines, with WT gDNA at ratios of 50%, 25%, 12.5%, 2.5%, 1.25%, 0.5%, 0.25%, 0.125%, and 0.05% (see FIG. 2C for exon 9 1633G>A, hotspot mutation and FIG. 2D for exon 20 3140A>G, hotspot mutation). The WT gDNA samples that were used for dilutions were selected to match mutated gDNA quantity, quality, and quantification cycle (Cq), to minimize PCR bias. Melting curves were generated and the ability to discriminate melting transitions of the cell line dilutions from that of WT sample was assessed. For exon 9, it was possible to clearly discriminate a dilution corresponding to 0.05% of MCF-7 cell line (FIG. 2C), while for exon 20, it could also discriminate a ratio of 0.05% of T47D cell line dilution (FIG. 2D). Melting curves were highly reproducible.

For both exons, PIK3CA mutations are detected by the derivative melting of the unlabeled blocking probe and mutant PIK3CA sequence, as amplified with the mutant allele-specific primer. Mutations are detected only if this peak at 60° C. is present. The other peak at higher temperatures is due to the PCR product and can be seen for both the mutant and WT, in case that there is a nonspecific amplification of the WT, by using the mutant allele-specific primer.

Especially, to get reliable information for the molecular characterization of CTCs, sensitivity, specificity, and robustness of the mutation detection systems used is extremely important. A highly sensitive method for PIK3CA mutations has been developed, based on HRMA [Vorkas P A, et al. PIK3CA hotspot mutation scanning by a novel and highly sensitive high-resolution small amplicon melting analysis method. J Mol Diagn 2010; 12:697-704], Despite the fact that this method is much more sensitive (1%) than the traditional Sanger sequencing, when this assay was applied in CTCs samples, the detection of mutations in CTCs failed.

EXAMPLE 4

Detection of PIK3CA Mutations in EpCAM Positive CTCs of Breast Cancer Patients with Clinically Confirmed Metastasis and Primary Tissues (FFPEs)

As a training group, 37 peripheral blood samples from patients with clinically confirmed metastasis and 15 primary breast tumor tissues (FFPEs) for PIK3CA mutations were analyzed. PIK3CA mutations were detected in 6/37 patients (16.2%) for exon 9 and 4/37 patients (10.8%) for exon 20, in the EpCAM-positive CTC fractions. In total, PIK3CA mutations were detected in 10/37 (27.0%) patients with metastatic breast cancer. In the primary breast tumor tissues, PIK3CA mutations were detected in 9/15 (60.0%) for exon 9 and 7/15 (46.7%) for exon 20. There were six cases where both hotspot mutations were detected in the same FFPE sample; in total, PIK3CA mutations were detected in 10/15 (66.7%) FFPE samples.

EXAMPLE 5

Independent group. Subsequently, the assay was evaluated in an independent group of 118 patients with operable breast cancer and 57 patients with clinically confirmed metastasis. For 76 of these patients with breast cancer, FFPEs from the primary tumor were also available.

Detection of PIK3CA Mutations in CTCs of Operable Breast Cancer Patients

Figure 3A:
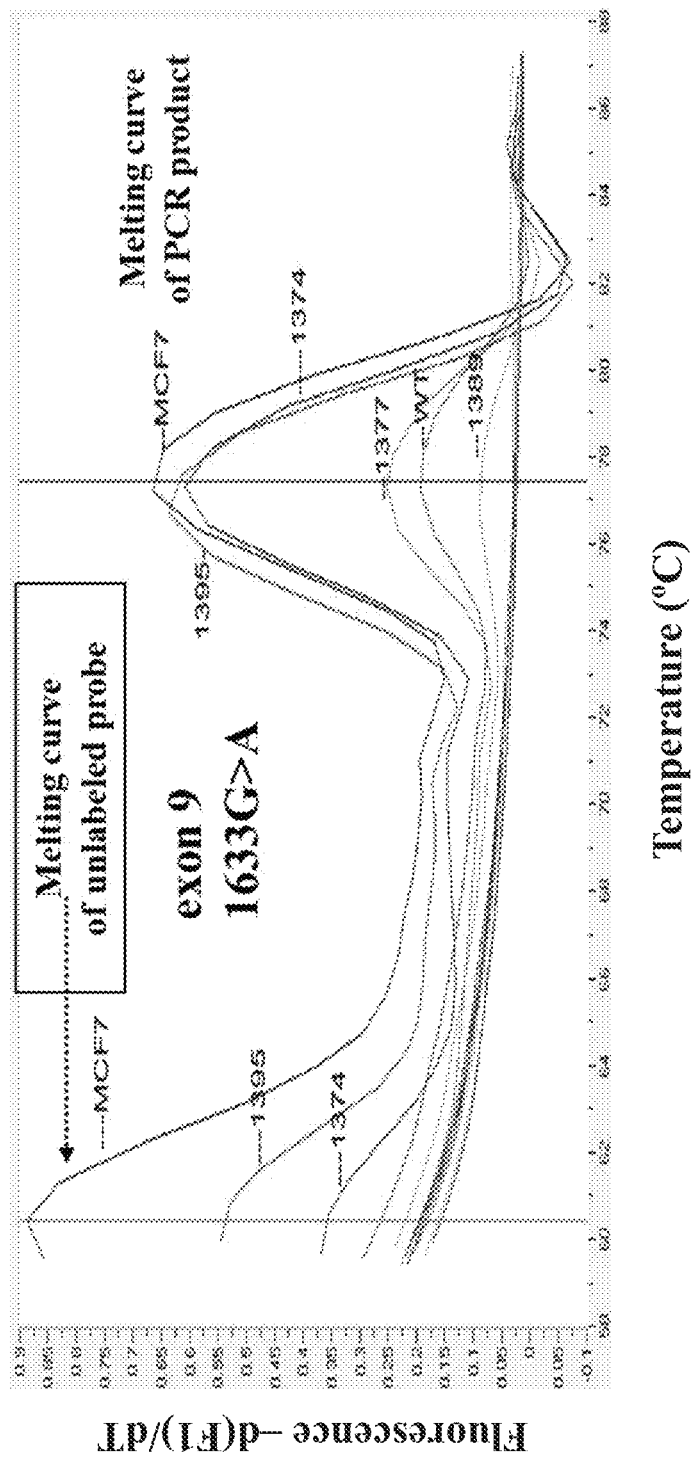
FIG. 3A-D shows the detection of PIK3CA mutations in CTC in patients with operable breast cancer for exon 9 1633 G>A (A) and for exon 20 3140 A>G (B). The detection of PIK3CA mutations in CTC in patients with clinically confirmed metastasis for exon 9 1633 G>A (C) and for exon 20 3140 A>G (D).
Figure 3B:
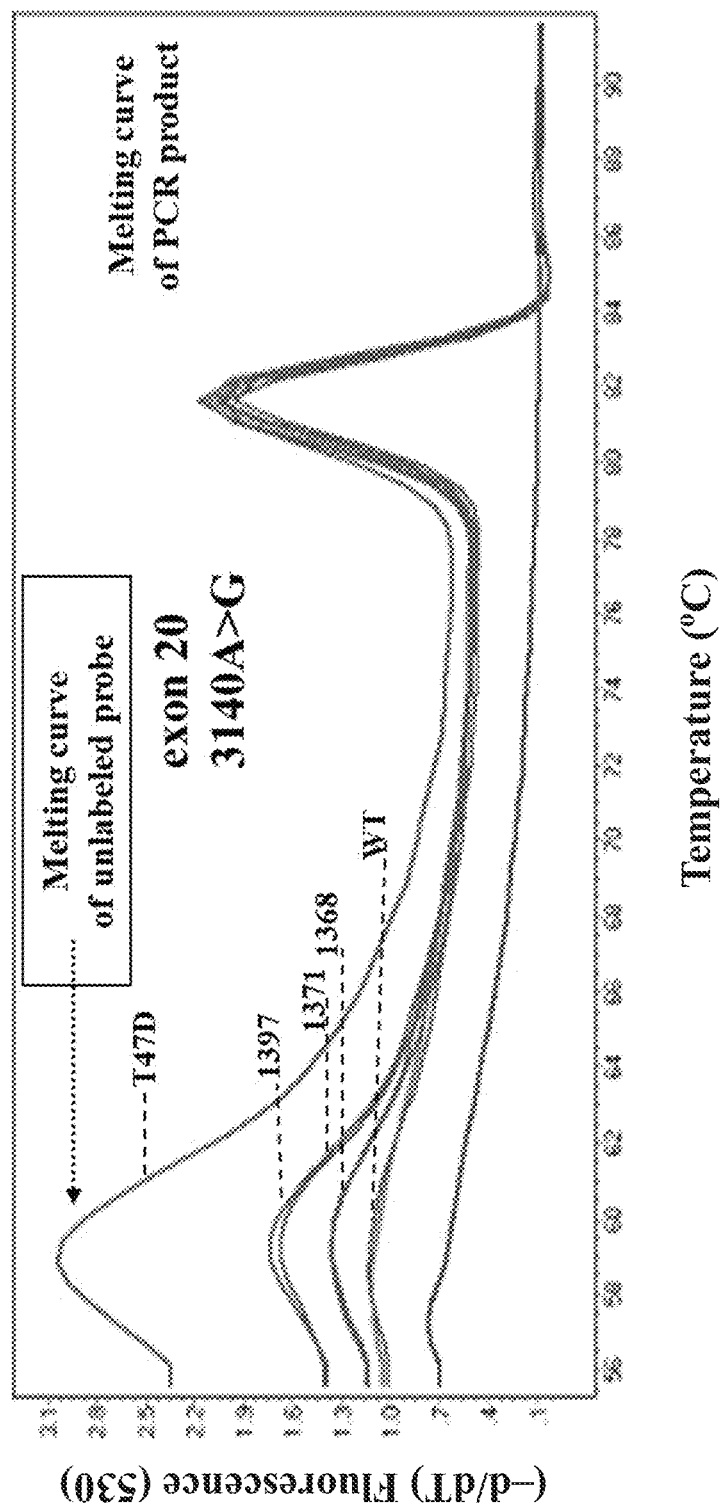

In the independent group, the EpCAM-positive CTC fractions from 118 patients with operable breast cancer after the primary cancer had been removed and before adjuvant chemotherapy had been initiated were analyzed. PIK3CA mutations were detected in 3/118 (2.5%) for exon 9 1633G>A (A), hotspot mutation (FIG. 3A) as well as in 21/118 (17.8%)

for exon 20 3140A>G, hotspot mutation (FIG. 3b). There was one case where both hotspot mutations were detected in the CTC sample. In total, PIK3CA mutations were detected in 24/118 (20.3%) of operable breast cancer patients. Baseline is PCR negative control.

Figure 3C:
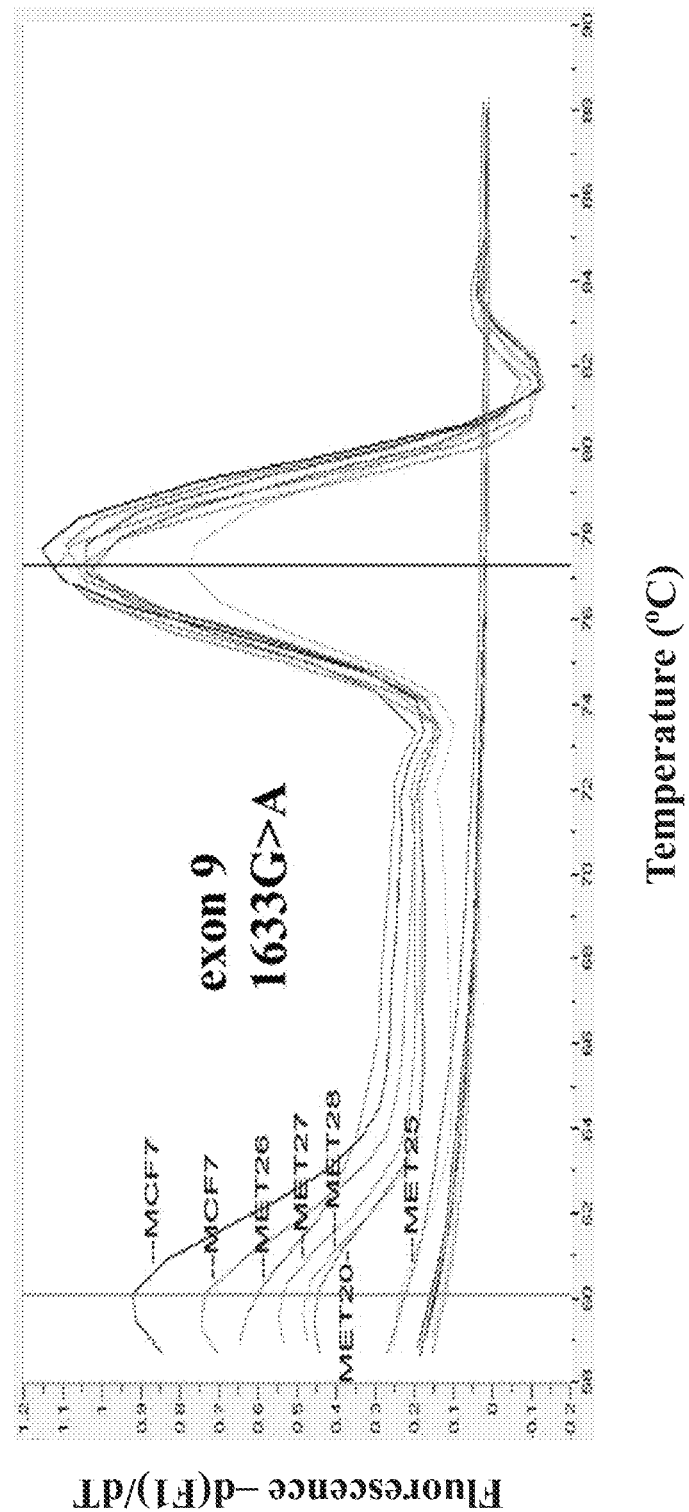
Figure 3D:
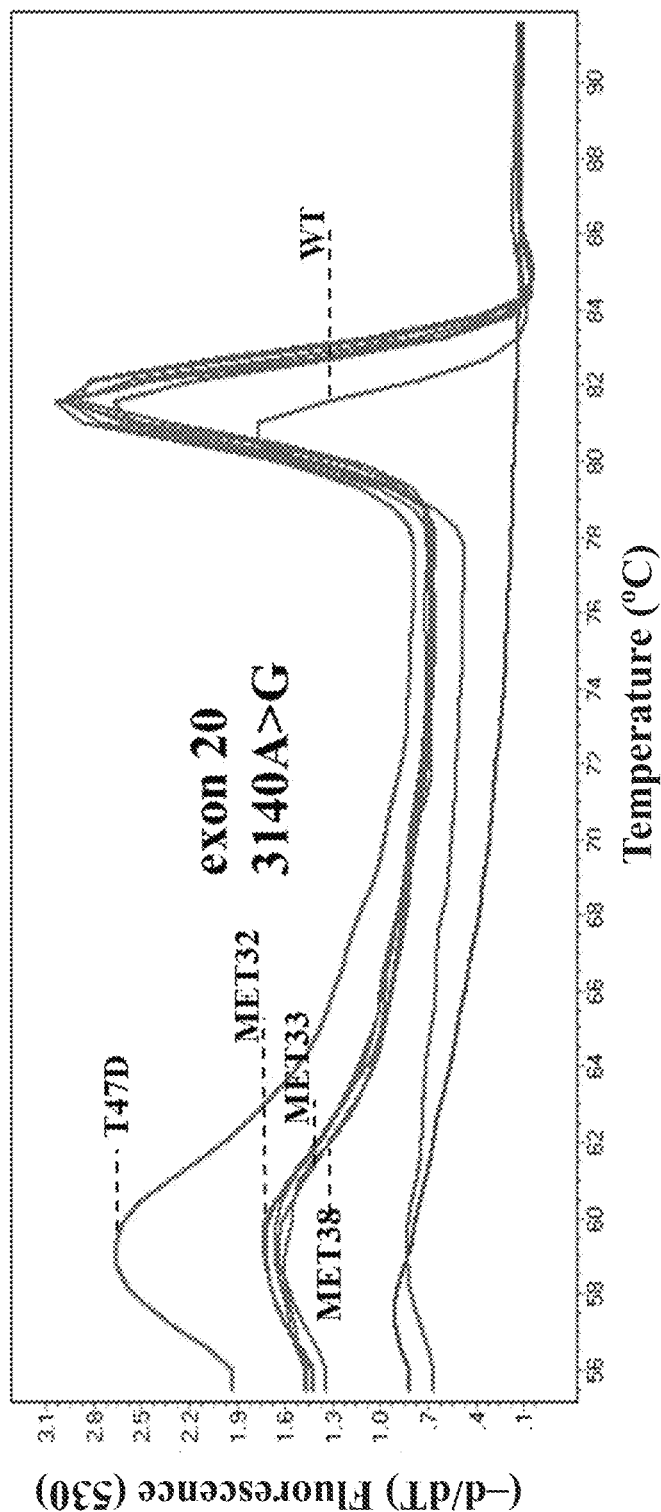

Detection of PIK3CA Mutations in CTCs of Breast Cancer Patients with Clinically Confirmed Metastasis In the independent group, the EpCAM-positive CTC fractions from 57 patients with metastatic breast cancer were analyzed. From these 57 patients, 24 had bone metastasis, 3 in the liver, 2 in the brain, 9 in the lung, 3 both bone and liver, and 6 both in the lung and bone and 2 in more than two different sites. PIK3CA mutations were detected in 8/57 (14.0%) for exon 9 1633G>A, hotspot mutation (FIG. 3C) and in 12/57 (21.1%) for exon 20 3140A>G, hotspot mutation, in the EpCAM-positive CTC fractions (FIG. 3D). In total, PIK3CA mutations were detected in 20/57 (35.1%) in this group of patients. The peaks at 60° C. in the melting curves in FIG. 3C and 3D indicate the presence of exon 9 and exon 20 mutations, respectively. In this context, if no peak is detected at 60° C., the sample is considered as wild-type for the mutation examined. Baseline is PCR negative control.

Detection of PIK3CA Mutations in Corresponding Primary Tumors

In the independent group, the PIK3CA mutational status in CTCs and corresponding primary tumors was compared in 76 patients with breast cancer (32 with clinically confirmed metastasis and 44 with operable breast cancer) as for these patients corresponding FFPEs were also available (Table 4).

TABLE 4

Independent group: PIK3CA mutational status in CTC and corresponding primary tumors (FFPEs)

| | | PIK3CA mutations in CTC exon 9,1633 G > A | | PIK3CA mutations in CTC exon 20, 3140 A > G | |
|---|---|---|---|---|---|
| PIK3CA mutations in primary tumors (FFPEs) | | | | | |
| Early breast cancer, (n = 44) | | | | | |
| | | CTC pos | CTC neg | CTC pos | CTC neg |
| FFPEs | pos | 0 | 21 | 2 | 3 |
| | neg | 1 | 22 | 8 | 31 |
| Concordance % | | 22/44 = 50% | | 33/44 = 75% | |
| P | | P = 0.523 | | P = 0.317 | |
| Cohen's kappa coefficient | | k = 0.045 | | k = 0.136 | |
| Clinically confirmed metastasis, (n = 32) | | | | | |
| | | CTC pos | CTC neg | CTC pos | CTC neg |
| FFPEs | pos | 4 | 13 | 2 | 6 |
| | neg | 1 | 14 | 2 | 22 |
| Concordance % | | 18/32 = 56.2% | | 24/32 = 75% | |
| P | | P = 0.208 | | P = 0.254 | |
| Cohen's kappa coefficient | | k = 0.161 | | k = 0.200 | |
| All patients, (n = 76) | | | | | |
| | | CTC pos | CTC neg | CTC pos | CTC neg |
| FFPEs | pos | 4 | 34 | 4 | 9 |
| | neg | 2 | 36 | 10 | 53 |
| Concordance % | | 40/76 = 52.6% | | 57/76 = 75% | |
| P | | P = 0.337 | | P = 0.188 | |
| Cohen's kappa coefficient | | k = 0.053 | | k = 0.145 | |

Exon 9, 1633G>A. Concerning all patients, the exon 1633G>A hotspot mutation was observed in 38/76 (50%) of the primary tumor samples and in 6 of 76 (7.9%) corresponding EpCAM-positive CTC fraction samples. For 4 patients that were carrying this PIK3CA hotspot mutation in their primary tumor, the identical mutation was also detected in the CTCs. In 34 patients, this mutation was identified in the primary tumor, but not in the EpCAM-positive CTC fraction, whereas 36 patients were found negative for this mutation both in the primary tumor and in the CTCs. However, in two cases, this hotspot mutation was identified in the EpCAM-positive CTC fraction, but not in the corresponding primary tumor. In patients with operable breast cancer, 1633G>A was observed in 21/44 (47.7%) of FFPEs and in 1/44 (2.3%) corresponding CTC samples; none of the patients carrying this PIK3CA hotspot mutation in her primary tumor had the identical mutation in CTC. In 21 patients, this mutation was identified in the primary tumor, but not in CTCs, whereas 22 patients were found negative for this mutation both in the primary tumor and in CTCs. However, in one case, this hotspot mutation was identified in the CTC fraction, but not in the corresponding primary tumor. In patients with metastasis, 1633G>A was observed in 17/32 (53.1%) of FFPEs and in 5/32 (15.6%) corresponding CTCs. For 4 patients that were carrying this PIK3CA hotspot mutation in their primary tumor, the identical mutation was also detected in the CTCs. In 13 patients, this mutation was identified in the primary tumor, but not in CTCs, while 14 patients were found negative for this mutation both in the primary tumor and in the CTCs. However, in one case, this hotspot mutation was identified in the CTC fraction, but not in the corresponding primary tumor.

Exon 20, 3140 A>G. Concerning all patients, exon 20 3140 A>G hotspot mutation was observed in 13/76 (17.1%) of FFPEs and in 14/76 (18.4%) corresponding CTC samples. For 4/13 patients that were carrying this PIK3CA hotspot mutation in their primary tumor, the identical mutation was also detected in the EpCAM-positive CTC fraction. In 9 patients, this mutation was identified in the primary tumor, but not in CTCs, whereas 53 patients were found negative for this mutation both in the primary tumor and in CTCs. It is remarkable that in 10 patients this hotspot mutation was detected only in the EpCAM-positive CTC fraction, but not in the corresponding primary tumor. In the group of patients with operable breast cancer, 3140 A>G was observed in 5/44 (11.4%) of FFPEs and in 10/44 (22.7%) corresponding CTCs. For 2/5 patients that were carrying this PIK3CA hotspot mutation in their primary tumor, the identical mutation was also detected in CTCs. In 3 patients, this mutation was identified in the primary tumor but not in CTCs, whereas 31 patients were found negative for this mutation both in the primary tumor and in CTCs. However, in 8 patients, this hotspot mutation was detected only in CTCs, but not in corresponding FFPEs. In the group of patients with metastasis, 3140 A>G was observed in 8/32 (25.0%) of the primary tumor samples and in 4/32 (12.5%) corresponding CTCs. For 2/8 patients that were carrying this PIK3CA hotspot mutation in their primary tumor, the identical mutation was also detected in CTCs. In 6 patients, this mutation was identified in the primary tumor, but not in CTCs, whereas 22 patients were found negative for this mutation both in the primary tumor and in the CTCs. However, in 2 patients, this hotspot mutation was detected only in CTC, but not in the corresponding primary tumor.

There was no concordance between the presence of both these hotspot PIK3CA mutations in primary tumors and corresponding CTC, as this was statistically evaluated separately for operable and metastasis verified breast cancer patients, or for all patients together (see Table 4).

The findings suggest that PIK3CA mutational status in CTCs can change during disease recurrence or progression in patients with breast cancer. When the PIK3CA mutational status in CTCs and the corresponding primary tumors in a subgroup of 76 patients were compared, it was observed that the same mutation was present both in the primary tumor and in CTCs in a minority of samples. In most patients, the mutation was identified in the primary tumor but not in CTCs, whereas many patients were negative for this mutation both in primary tumor and in CTCs. However, there were 12 cases where the hotspot mutations were identified in CTCs, but not in the corresponding primary tumor; in two patients, 1633 G>A was observed in CTCs, but not in corresponding FFPEs, whereas in 10 patients 3140 A>G was observed in CTCs, but not in corresponding primary tumor. Similar findings, reflecting the heterogeneity of CTCs have been reported.

EXAMPLE 6

PIK3CA Mutation Status in CTCs in Respect to CK-19 mRNA Expression

In the independent group, it was further evaluated whether PIK3CA mutational status in CTCs is correlated with CK-19 mRNA expression, for 157 of these patients (57 with clinical metastasis and 100 with early breast cancer; Table 5). The detection of CK-19 mRNA-positive cells in the peripheral blood is the most sensitive biomarker for occult tumor cells in operable and metastatic breast cancer.

$11/57$ (19.3%) samples were positive both for PIK3CA mutations and CK-19 expression, 6 in exon 9 and 5 in exon 20. There were $14/57$ (24.6%) samples positive for CK-19, not carrying these hotspot mutations in PIK3CA. It is highly remarkable that PIK3CA hotspot mutations were identified in CTCs of 9 patients who were negative for CK-19 mRNA expression. These 26 samples (17 from patients with operable breast cancer and 9 from patients with clinically confirmed metastasis) that were found positive for PIK3CA mutations in CTC, but were negative for CK-19 mRNA expression, would have been characterized as CTC-negative if PIK3CA mutations were not detected. There was no concordance concerning the presence of both these hotspot PIK3CA mutations and CK-19 mRNA expression in CTCs (see Table 2).

An important observation of this study was that a significant number of patients ($17/118$ in the operable breast cancer group and $9/57$ in the metastasis verified group) that were negative for CK-19 mRNA expression were carrying PIK3CA hotspot mutations in CTCs. These patients would have been characterized as CTC-negative if PIK3CA mutations were not detected. Molecular characterization of CTCs has demonstrated that CTC are highly heterogeneous. This could be, at least part, attributed to epithelial-mesenchymal transition and mesenchymal-epithelial transition. In this

TABLE 5

Independent group: comparison between PIK3CA mutations in CTC and CK-19 expression

| Patients | | PIK3CA mutations in CTC exon 9, 1633G > A | | PIK3CA mutations in CTC exon 20, 3140A > G | | PIK3CA mutations in CTC At least one mutation | |
|---|---|---|---|---|---|---|---|
| Early breast cancer, (n = 100) | | | | | | | |
| | | pos | neg | pos | neg | pos | neg |
| CK-19 | pos | 0 | 36 | 3 | 33 | 3 | 33 |
| | neg | 2 | 62 | 15 | 49 | 17 | 47 |
| Concordance (%) | | 62/100 (62%) | | 52/100 (52%) | | 50/100 (50%) | |
| P | | P = 0.407 | | P = 0.049 | | P = 0.023 | |
| Cohen's kappa coefficient | | k = 0.59 | | k = 0.49 | | k = 0.46 | |
| Clinically confirmed metastasis Verified, (n = 57) | | | | | | | |
| | | pos | neg | pos | neg | pos | neg |
| CK-19 | pos | 6 | 19 | 5 | 20 | 11 | 14 |
| | neg | 2 | 30 | 7 | 25 | 9 | 23 |
| Concordance (%) | | 36/57 (63.2%) | | 30/57 (52.6%) | | 44/57 (77.2%) | |
| P | | P = 0.073 | | P = 0.564 | | P = 0.167 | |
| Cohen's kappa coefficient | | k = 0.61 | | k = 0.48 | | k = 0.52 | |
| All patients, (n = 157) | | | | | | | |
| | | pos | neg | pos | neg | pos | neg |
| CK-19 | pos | 6 | 55 | 8 | 53 | 14 | 47 |
| | neg | 4 | 92 | 22 | 74 | 26 | 70 |
| Concordance % | | 98/157 (62.4%) | | 82/157 (52.2%) | | 84/157 (53.5%) | |
| P | | P = 0.140 | | P = 0.093 | | P = 0.350 | |
| Cohen's kappa coefficient | | k = 0.61 | | k = 0.48 | | k = 0.48 | |

In operable breast cancer, only $3/100$ samples were positive for both PIK3CA mutations and CK-19 mRNA expression, all in exon 20. There were $33/100$ samples positive for CK-19, not carrying mutations in PIK3CA, while it is highly remarkable that PIK3CA hotspot mutations were identified in CTC of 17 patients who were negative for CK-19 mRNA expression. In patients with clinically confirmed metastasis, context, it is not expected that all CK-19-positive CTCs would be PIK3CA mutation-positive, or that all our samples that are CK-19-negative would not carry PIK3CA mutations in CTCs. The CK-19 real-time PCR assay is very specific and sensitive, and it has already been demonstrated in previous studies its clinical significance [Stathopoulou A, Vlachonikolis I, Mavroudis D, Perraki M, Kouroussis C, Apostolaki S, et al. Molecular detection of cytokeratin-19-positive cells in the peripheral blood of patients with operable breast cancer: evaluation of their prognostic significance. J Clin Oncol 2002; 20:3404-12.]. However, there is always a number of patients that do not relapse even if they are CK-79-positive, or do relapse even if they are CK-79-negative, and the same has been shown even when using the FDA-cleared CellSearch™ system, a clear indication that one marker is not a panacea and not enough to verify the presence of a malignant CTC population in our samples.

EXAMPLE 7

Figure 4:
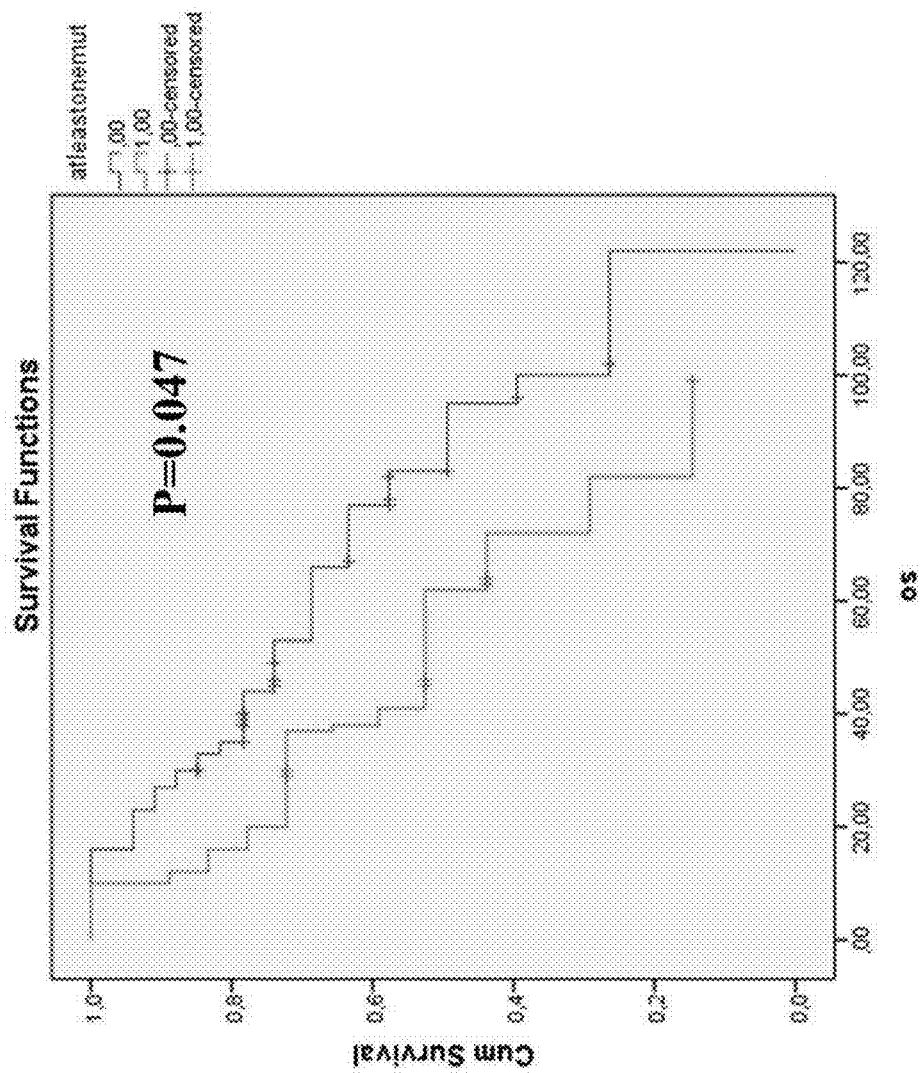
FIG. 4 depicts the Kaplan-Meier curve, which estimates of OS in months for patients with breast cancer with clinically confirmed metastasis, with respect to PIK3CA mutational status in CTCs.

Clinical Significance of PIK3CA Mutational Status in CTCs in Patients with Verified Metastasis The correlation between PIK3CA mutational status in CTCs and the clinical outcome of this relatively small group of patients with clinically confirmed metastasis were further evaluated. Kaplan-Meier survival analysis, performed by using patients' postoperative survival, demonstrated that patients who carried PIK3CA hotspot mutations on CTC (n=20) had a significant shorter OS than those without (n=37) (P=0.047, log-rank test; see FIG. 4).

A striking finding is also that the presence of PIK3CA mutations in CTCs is associated with worse survival in metastatic patients. This is the first time that the presence of gene mutations in CTCs is correlated with patient survival, in any type of cancer. Matching patients who have cancers with activating mutations in the PI3K signaling pathway to phase I protocols testing PI3K inhibitors have improved response rates and survival [Tsimberidou A M, et al. Personalized medicine in a phase I clinical trials program: the MD Anderson Cancer Center initiative. Clin Cancer Res 2012; 18: 6373-83]. In respect to this, our findings that PIK3CA mutations can be exclusively present in CTCs, while absent in the primary tumor, can be beneficial for patients, as was recently shown in a pilot prospective study where administration of herceptin was based on the presence of CK-19 mRNA-positive CTCs [Georgoulias V, et al. Trastuzumab decreases the incidence of clinical relapses in patients with early breast cancer presenting chemotherapy-resistant CK-19 mRNA-positive circulating tumor cells: results of a randomized phase II study. Ann Oncol 2012; 23:1744-50]. Mutations in the PI3K/AKT signaling pathway, which is frequently deregulated in tumor cells, have been recently identified in breast cancer stem cells that are thought to have a central role in the initiation, progression, and clinical response of breast cancer [Donovan C A, et al. Correlation of breast cancer axillary lymph node metastases with stem cell mutations. JAMA Surg 2013; 148:873-8],

EXAMPLE 8

Figure 5A:
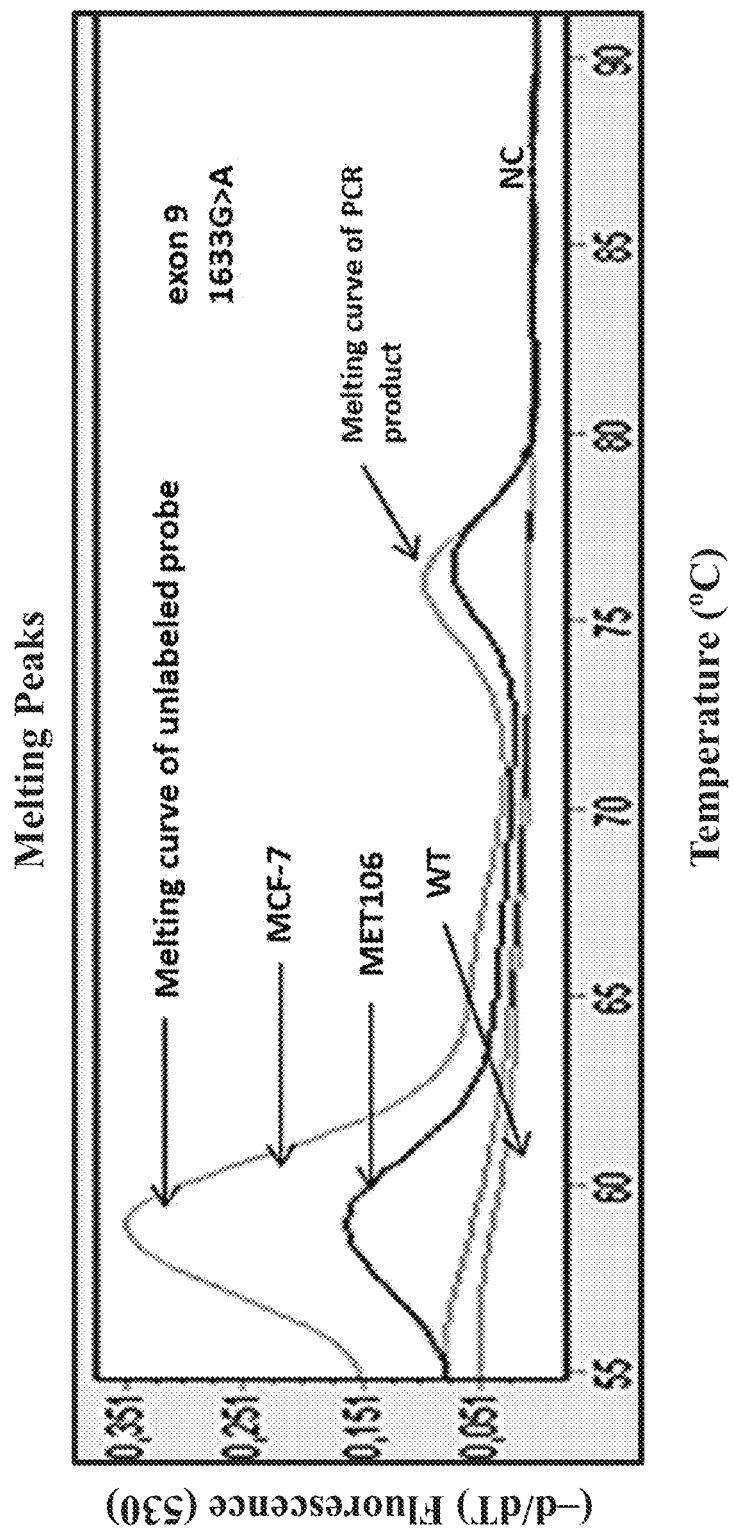
FIG. 5A-C shows the detection of PIK3CA mutations in cell free DNA in patients with clinically confirmed metastatic breast cancer for exon 9 1633 G>A (A,B) and for exon 20 3140 A>G (C).
Figure 5B:
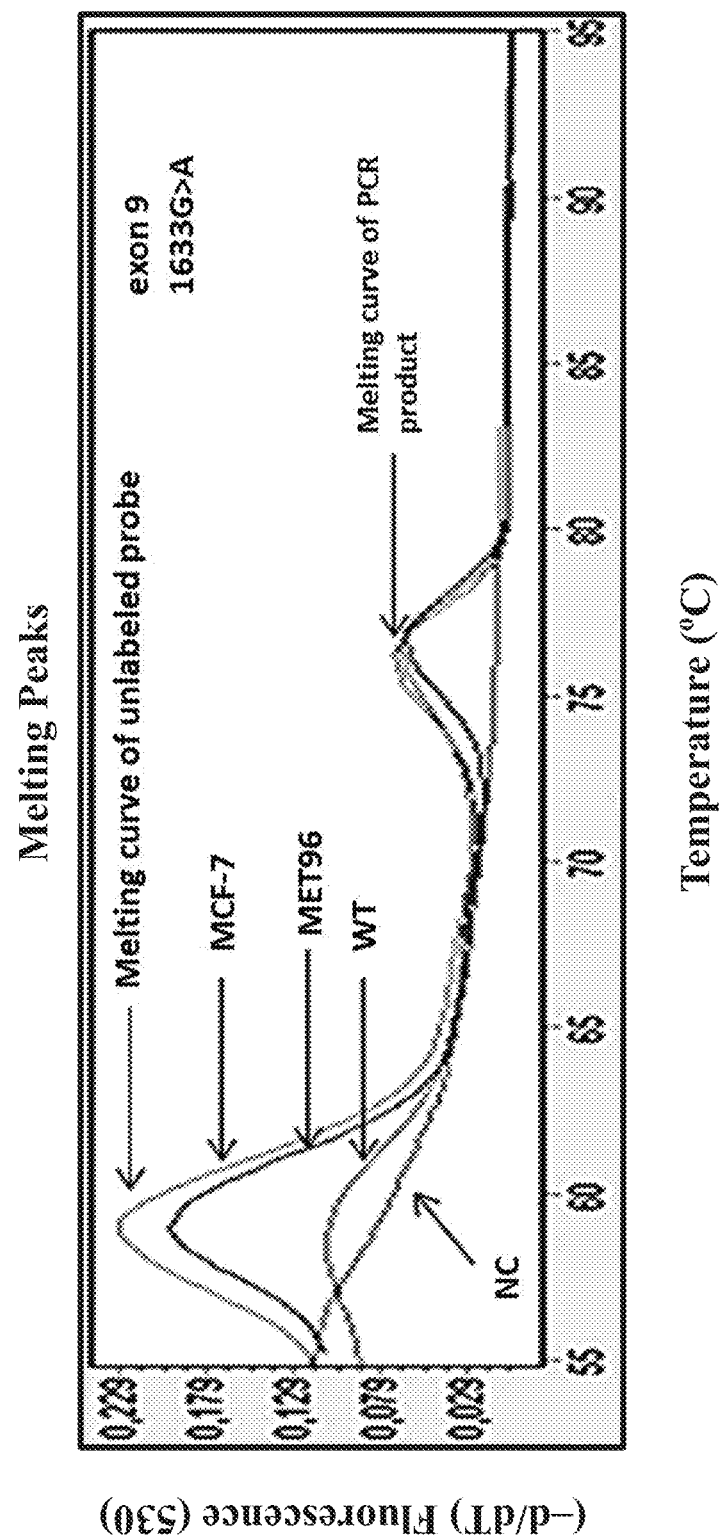
Figure 5C:
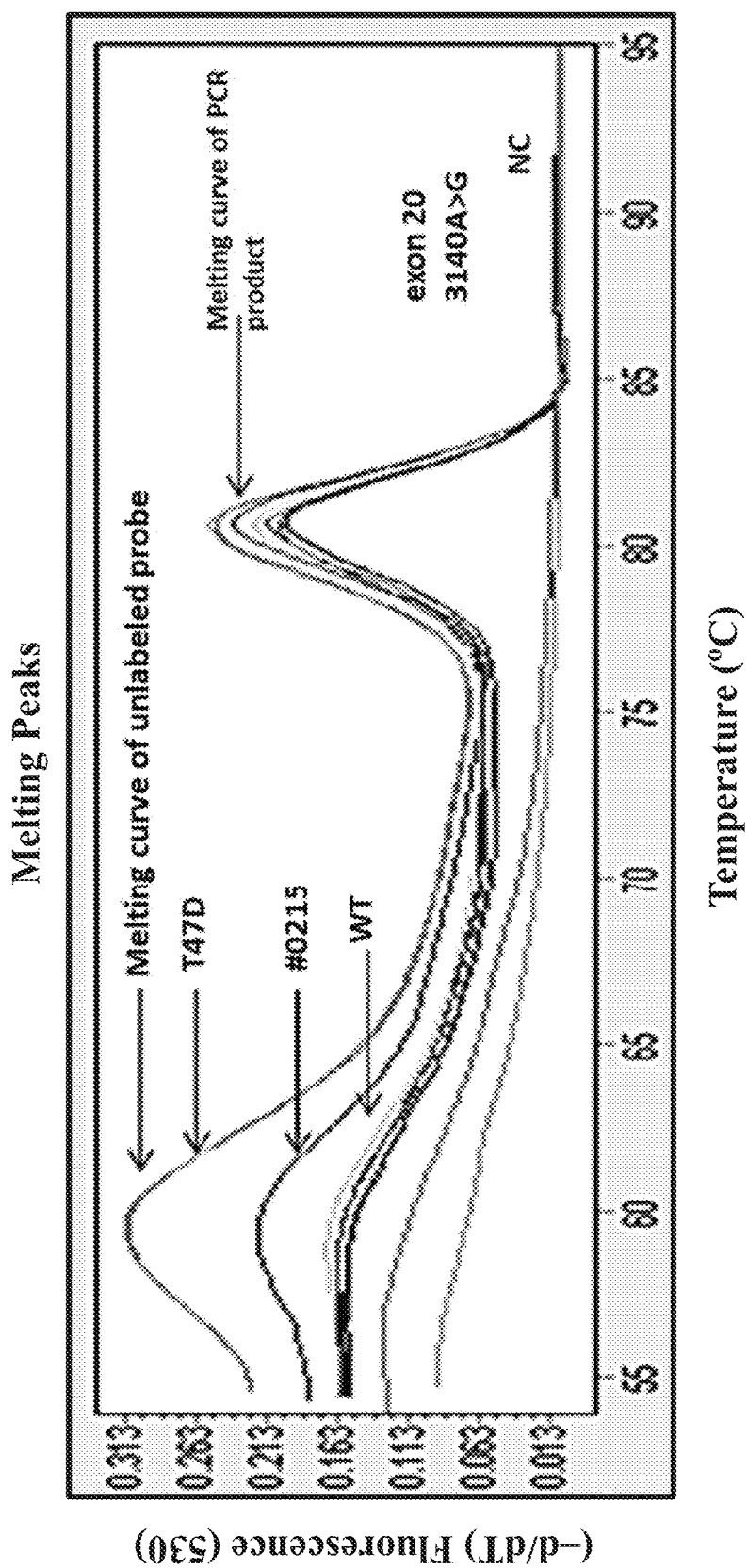
Figure 6A:
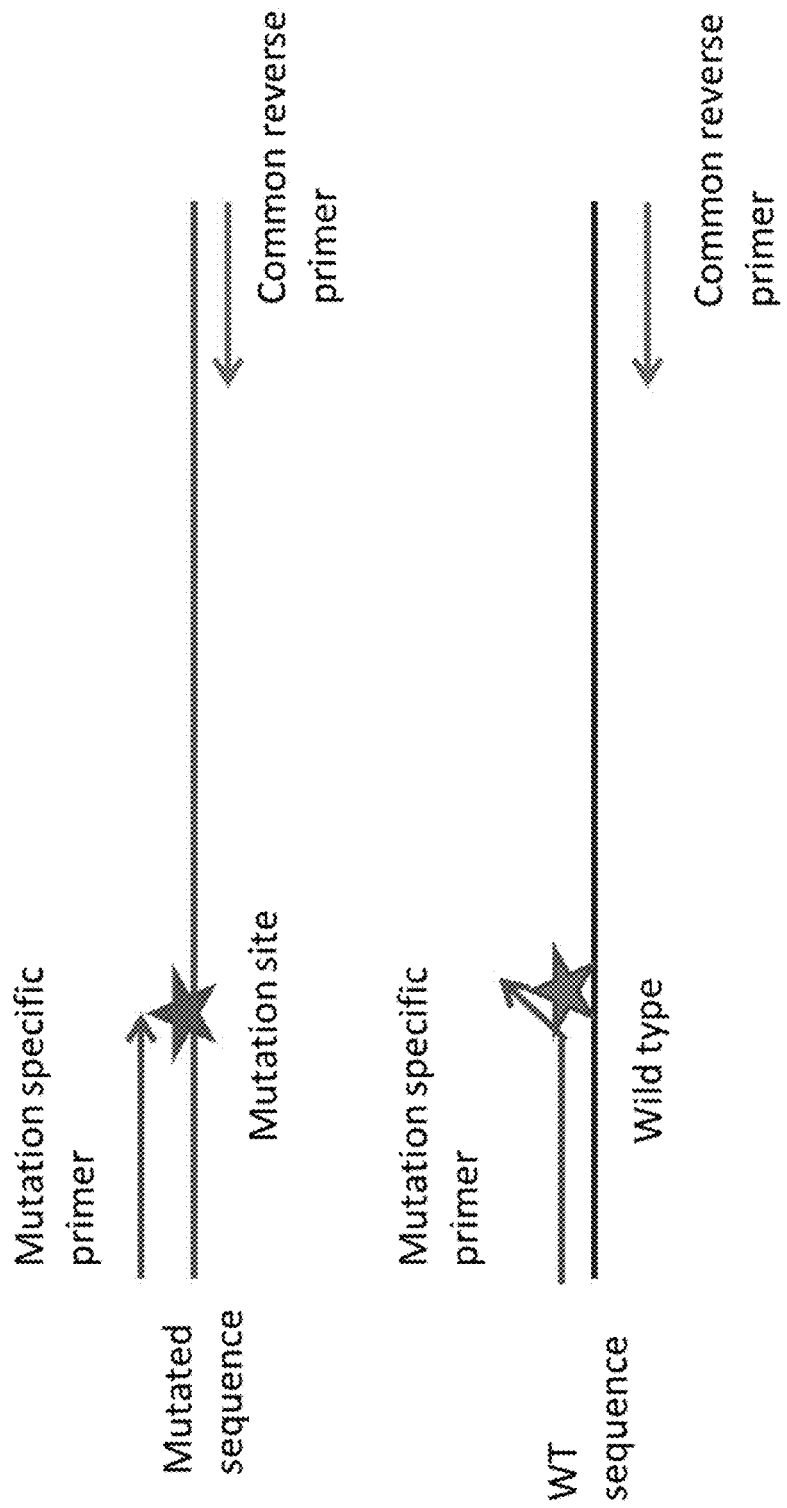
FIG. 6A-D presents the principle of the method, using only a mutation specific primer (A), using a mutation specific primer and a competitive, wild-type specific probe (B), preferential amplification of mutated sequences (C), and effect of mutation on melting temperature (D).
Figure 6B:
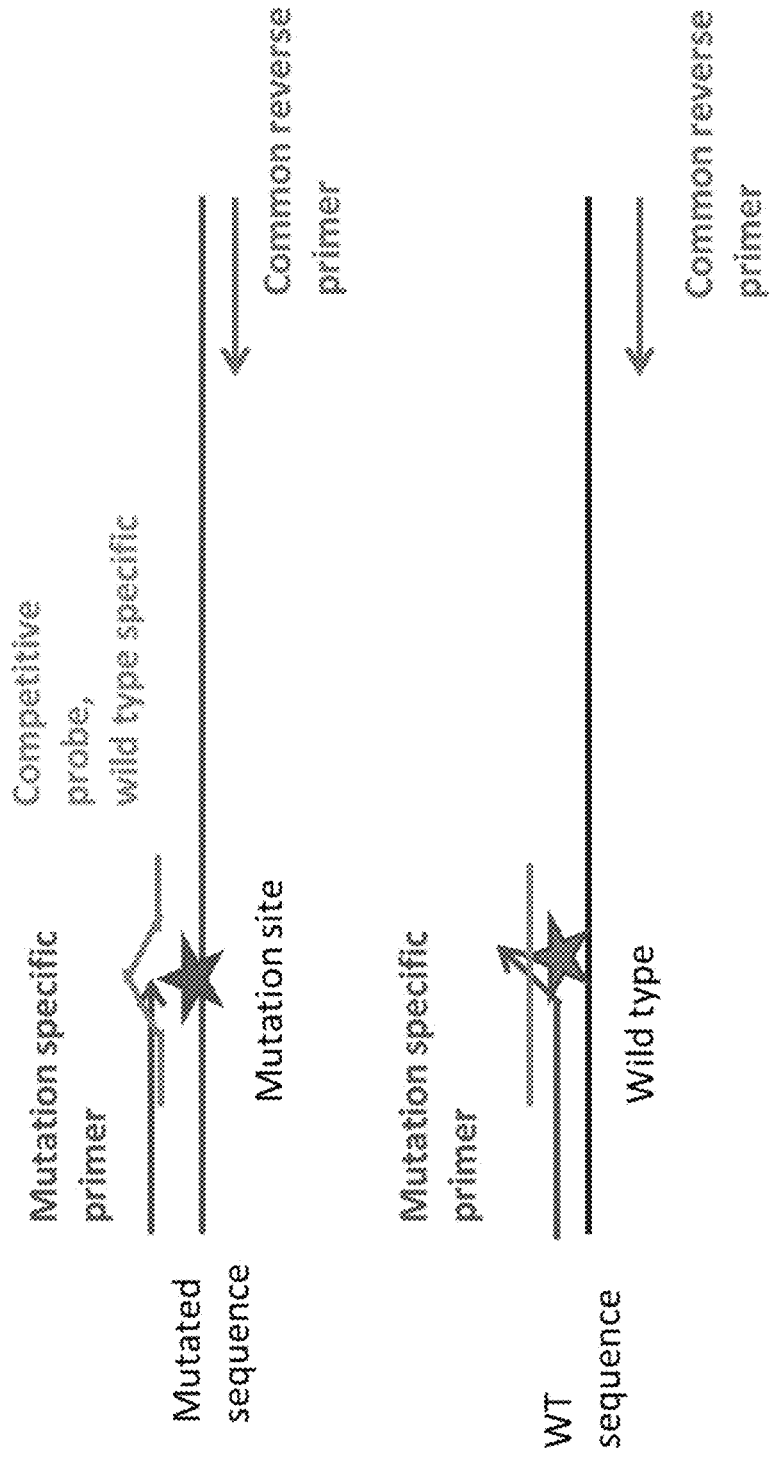
Figure 6C:
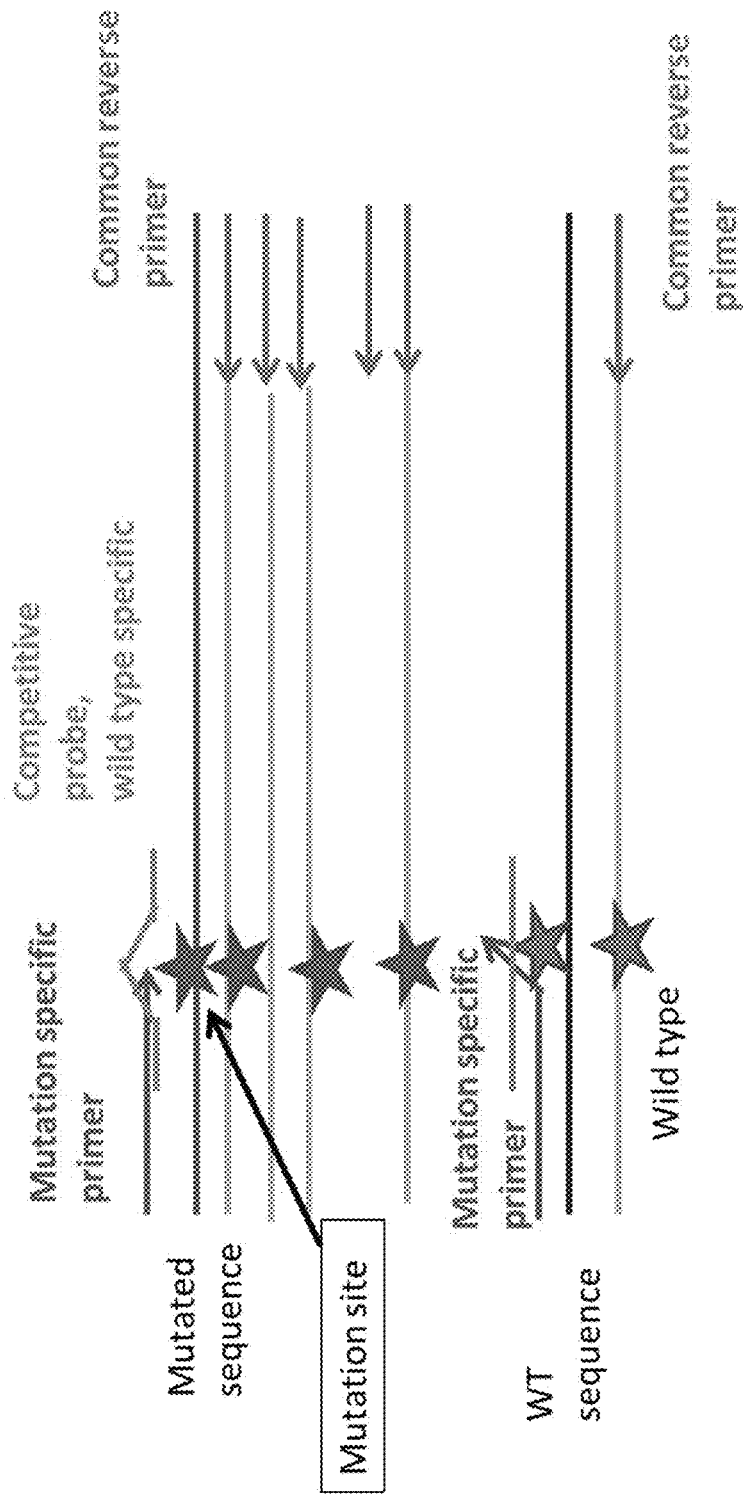
Figure 6D:
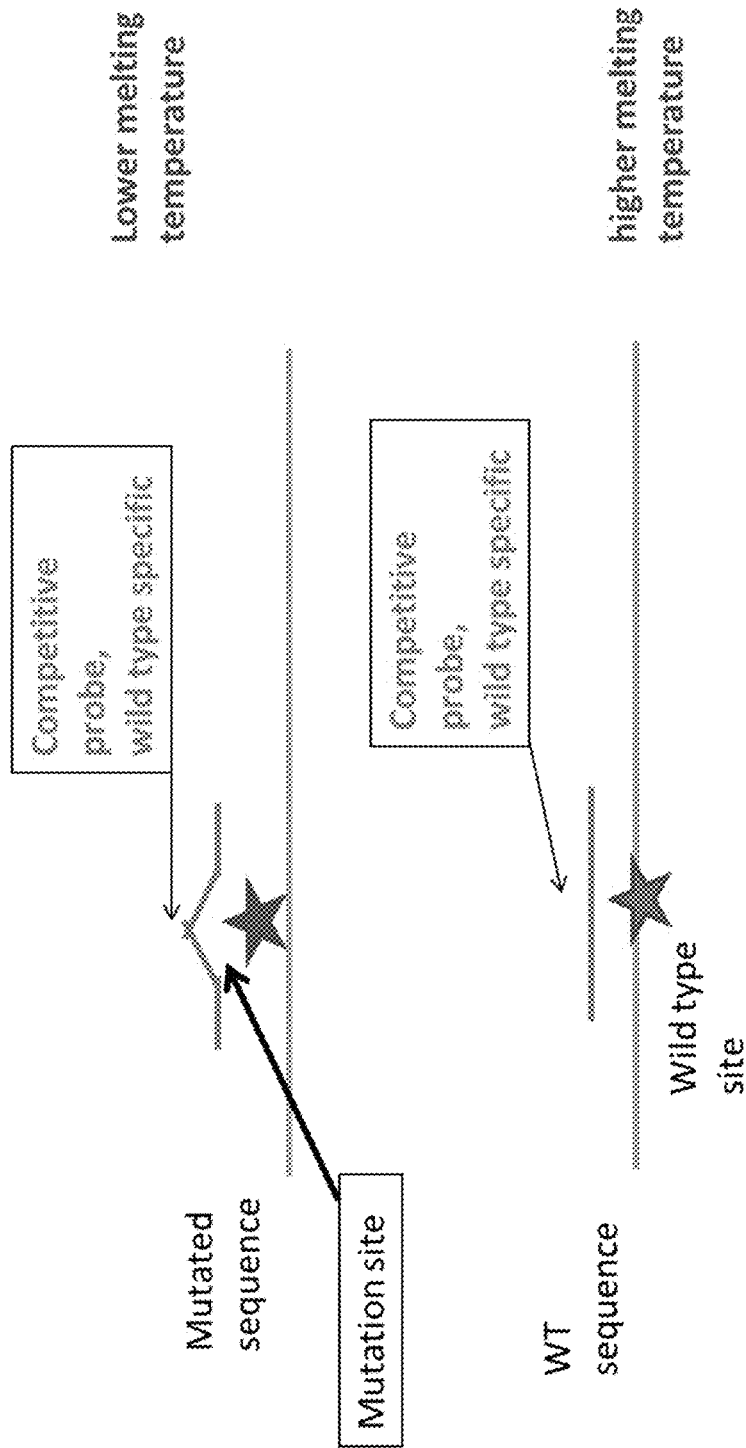

Detection of PIK3CA Mutations in ctDNA of Breast Cancer Patients with Verified Metastasis The developed method was used to detect hot spot PIK3CA mutations in ctDNA isolated from plasma of breast cancer patients with verified metastasis. First of all, all ctDNA samples extracted from plasma were examined for their DNA quality; to verify DNA quality, primers specific for the wild type in exactly the same PIK3CA gene region for exon 9 that were used to assess for hotspots mutations. The mutation status of PIK3CA gene in ctDNA samples was detected by the developed methodology exactly as previously described (FIG. 5). PIK3CA mutations were detected in 4/24 (16%) for exon 9 (FIG. 5A, 5B) and in 6/24 (25%) for exon 20 (FIG. 5C), in ctDNA samples. The peaks at 60° C. in the melting curves in FIGS. 5A, 5B and 5C indicate the presence of exon 9 and exon 20 mutations, respectively. In this context, if no peak is detected at 60° C., the sample is considered as wild-type for the mutation examined.

In this study demonstrated that this assay can detect PIK3CA mutations in ctDNA isolated from plasma of cancer patients. The assay sensitivity is extremely low (0.05%) and the specificity is very high; this assay can detect very rare PIK3CA mutant alleles in the presence of a high amount of wild type alleles. Overall, 4 out of 24 samples were positive for 1633 G>A mutation in exon 9 and 6 out of 24 were positive for 3140 A>G mutation in ctDNA isolated from plasma samples. Circulating tumor DNA appears to be an extremely effective and advantageous source of biomarkers for determining in real time the mutational status of tumors; however, in this case highly sensitive, robust and specific methodologies are needed. Here evidence provide that this assay offers a useful tool for the detection of PIK3CA mutations in ctDNA, isolated from plasma of cancer patients.

What is claimed is:

1. A method for analyzing presence of a PIK3CA mutant allele DNA in a DNA sample, said method comprising the steps of performing an asymmetric and allele specific Polymerase Chain Reaction (PCR) of said mutant allele DNA in the DNA sample, and performing a melting analysis of DNA produced in the PCR, wherein said PCR is carried out by the use of:

a mutant allele specific primer complementary to a 3' (three prime) end of a first strand of the mutant allele DNA to be amplified, said mutant allele specific primer comprises a mutation site and a mismatch to corresponding wild type DNA, an unlabeled blocking probe, comprising the sequence of SEQ ID NO: 15, that is an oligonucleotide complementary to a wild type sequence of a first strand of wild type DNA corresponding to a first strand of the mutant allele DNA at a corresponding position in which a mutation to be detected is present, said unlabeled blocking probe comprising an additional mismatch to said first strand of the mutant allele DNA besides the mutation site, and which probe is blocked from acting as a primer for DNA synthesis in the PCR reaction, and a common primer that is complementary to a 3' end of a second strand of the mutant allele DNA to be amplified by the PCR, and wherein said melting analysis is carried out by the use of:
the unlabeled blocking probe, which also functions as a melting probe, and
a detectable component for measuring a melting temperature of double-stranded DNA components at least including a first double-stranded component comprising the melting probe bound to an amplified mutant allele DNA strand or a second double-stranded component comprising the melting probe bound to a wild type allele DNA strand, wherein the melting temperature differs between the first double-stranded component and the second double-stranded component.

2. The method according to claim 1, wherein the mutant allele DNA to be amplified in the PCR reaction comprises exon 20 having the sequence according to SEQ ID NO: 2 of PIK3CA, and the H1047R mutant allele specific primer has the sequence according to SEQ ID NO: 13, which is complementary to a DNA strand of exon 20.

3. The method according to claim 1, wherein the mutation is present in exon 20 of PIK3CA, and the H1047R mutant allele specific primer comprises the sequence 5'-GAATGATGCTCG-3' the (SEQ ID NO: 16) or sequence 5'-ATGAAACAAATGAATGATGCTCG-3' (SEQ ID NO: 13), where G indicates a first mutation relative to wild type exon 20 and T indicates a second mutation relative to wild type exon 20.

4. The method according to claim 1, wherein the mutant allele DNA to be amplified in the PCR reaction comprises exon 20 having the sequence according to SEQ ID NO: 2 of PIK3CA, and the H1047L mutant allele specific primer has the sequence according to SEQ ID NO: 14, which is complementary to a DNA strand of exon 20.

5. The method according to claim 1, wherein the mutation is present in exon 20 of PIK3CA, and the H1047L mutant allele specific primer comprises the sequence 5'-GAAT-GATGCTCT-3' (SEQ ID NO: 17) or the sequence 5'-AT-GAAACAAATGAATGATGCTCI-3' (SEQ ID NO: 14), where I indicates a first mutation relative to wild type exon 20 and T indicates a second mutation relative to wild type exon 20.

6. The method according to claim 1, wherein the unlabeled blocking probe has a modified 3'-end that is modified by an added phosphate group as compared to a PCR primer for amplification.

7. The method according to claim 6, wherein the common primer has 75% to 100% identity to the sequence 5'-TCTCAGTTATCTTTTCAGTTCAATGC-3' (SEQ ID NO: 12).

8. The method according to claim 1, wherein the unlabeled blocking probe and the common primer is present at a higher concentration than the mutant allele specific primer.

9. A method for diagnosing malignant neoplastic disease in a mammalian subject having or being suspected of having a malignant neoplastic disease, the method comprising:
performing the method of claim 1,
by way of the melting analysis, determining the presence of PIK3CA mutations in the DNA sample, and
diagnosing the subject as having the malignant neoplastic disease when PIK3CA mutations are present in the DNA sample.

10. The method according to claim 9, wherein the malignant neoplastic disease is breast cancer, colon cancer, lung cancer, cervical cancer, ovarian cancer, esophageal cancer, brain cancer, skin cancer, liver cancer, pancreatic cancer, head and neck cancer, gastric cancer and thyroid cancer.

11. A method for predicting the efficacy of a treatment for a malignant neoplastic disease in a subject, the method comprising:
obtaining a DNA sample from a subject,
performing the method according to claim 1 on the DNA sample,
detecting a presence of PIK3CA mutant allele DNA in the DNA sample,
repeating the obtaining the DNA sample, the performing the method, and the detecting at one or more time points during the treatment of the subject, and
determining that the treatment is effective when a relative presence of the PIK3CA mutant allele DNA decreases over time.

12. A method of predicting an outcome of a treatment in a subject suffering from malignant neoplastic disease, the method comprising:
obtaining a DNA sample from a subject,
performing the method according to claim 1 on the DNA sample,
detecting a presence of PIK3CA mutant allele DNA in the DNA sample,
comparing the amount of the PIK3CA mutant allele DNA detected in the DNA sample to at least one of a positive control or a negative control, and
predicting the outcome of the treatment from the comparing.

13. A method of assessing a recurrence of a malignant neoplastic disease in a subject, the method comprising:
obtaining a DNA sample from a subject,
performing the method according to claim 1 on the DNA sample,
detecting a presence of PIK3CA mutant allele DNA in the DNA sample,
repeating the obtaining the DNA sample, the performing the method, and the detecting at one or more time points post treatment of the subject, and
determining a recurrence of the malignant neoplastic disease when a relative presence of the PIK3CA mutant allele DNA in the DNA sample increases over time.

14. The method according to claim 1, wherein the method has an assay sensitivity of 0.05%.

* * * * *

SEQUENCE LISTING

```
<160> NUMBER OF SEQ ID NOS: 17

<210> SEQ ID NO 1
<211> LENGTH: 125
<212> TYPE: DNA
<213> ORGANISM: Homo sapiens

<400> SEQUENCE: 1
agtaacagac tagctagaga caatgaatta agggaaaatg acaaagaaca gctcaaagca      60
atttctacac gagatcctct ctctgaaatc actaagcagg agaaagattt tctatggagt     120
cacag                                                                125

<210> SEQ ID NO 2
<211> LENGTH: 619
<212> TYPE: DNA
<213> ORGANISM: Homo sapiens

<400> SEQUENCE: 2
```

-continued

```
gtttcaggag atgtgttaca aggcttatct agctattcga cagcatgcca atctcttcat    60
aaatcttttc tcaatgatgc ttggctctgg aatgccagaa ctacaatctt ttgatgacat   120
tgcatacatt cgaaagaccc tagccttaga taaaactgag caagaggctt tggagtattt   180
catgaaacaa atgaatgatg cacgtcatgg tggctggaca acaaaaatgg attggatctt   240
ccacacaatt aaacagcatg cattgaactg aaaagataac tgagaaaatg aaagctcact   300
ctggattcca cactgcactg ttaataactc tcagcaggca agaccgatt gcataggaat    360 tgcacaatcc atgaacagca ttagaattta cagcaagaac agaaataaaa tactatataa   420
tttaaataat gtaaacgcaa acagggtttg atagcactta aactagttca tttcaaaatt   480
aagctttaga ataatgcgca atttcatgtt atgccttaag tccaaaaagg taaactttga   540
agattgtttg tatcttttt taaaaaacaa aacaaaacaa aaatccccaa aatatataga    600
aatgatggag aaggaaaaa                                                619
```

<210> SEQ ID NO 3
<211> LENGTH: 12
<212> TYPE: DNA
<213> ORGANISM: Artificial Sequence
<220> FEATURE:
<223> OTHER INFORMATION: primer for PCR

<400> SEQUENCE: 3

```
tttctcctga tt                                                        12
```

<210> SEQ ID NO 4
<211> LENGTH: 27
<212> TYPE: DNA
<213> ORGANISM: Artificial Sequence
<220> FEATURE:
<223> OTHER INFORMATION: (primer)

<400> SEQUENCE: 4

```
actccataga aaatctttct cctgatt                                        27
```

<210> SEQ ID NO 5
<211> LENGTH: 11
<212> TYPE: DNA
<213> ORGANISM: Artificial Sequence
<220> FEATURE:
<223> OTHER INFORMATION: (probe)

<400> SEQUENCE: 5

```
ctgatcagtg a                                                         11
```

<210> SEQ ID NO 6
<211> LENGTH: 26
<212> TYPE: DNA
<213> ORGANISM: Artificial Sequence
<220> FEATURE:
<223> OTHER INFORMATION: (probe)

<400> SEQUENCE: 6

```
ctttctcctg atcagtgatt tcagag                                         26
```

<210> SEQ ID NO 7
<211> LENGTH: 24
<212> TYPE: DNA
<213> ORGANISM: Artificial Sequence
<220> FEATURE:
<223> OTHER INFORMATION: (primer)

<400> SEQUENCE: 7
gctcaaagca atttctacac gaga                                          24

<210> SEQ ID NO 8
<211> LENGTH: 11
<212> TYPE: DNA
<213> ORGANISM: Artificial Sequence
<220> FEATURE:
<223> OTHER INFORMATION: (primer)

<400> SEQUENCE: 8
aatgatgcac g                                                        11

<210> SEQ ID NO 9
<211> LENGTH: 23
<212> TYPE: DNA
<213> ORGANISM: Artificial Sequence
<220> FEATURE:
<223> OTHER INFORMATION: (primer)

<400> SEQUENCE: 9
atgaaacaaa tgaatgatgc acg                                           23

<210> SEQ ID NO 10
<211> LENGTH: 11
<212> TYPE: DNA
<213> ORGANISM: Artificial Sequence
<220> FEATURE:
<223> OTHER INFORMATION: (probe)

<400> SEQUENCE: 10
tgcacatcat g                                                        11

<210> SEQ ID NO 11
<211> LENGTH: 21
<212> TYPE: DNA
<213> ORGANISM: Artificial Sequence
<220> FEATURE:
<223> OTHER INFORMATION: (probe)

<400> SEQUENCE: 11
gaatgatgca catcatggtg g                                             21

<210> SEQ ID NO 12
<211> LENGTH: 26
<212> TYPE: DNA
<213> ORGANISM: Artificial Sequence
<220> FEATURE:
<223> OTHER INFORMATION: (primer)

<400> SEQUENCE: 12
tctcagttat cttttcagtt caatgc                                        26

<210> SEQ ID NO 13
<211> LENGTH: 23
<212> TYPE: DNA
<213> ORGANISM: Artificial Sequence
<220> FEATURE:
<223> OTHER INFORMATION: (primer)

<400> SEQUENCE: 13
atgaaacaaa tgaatgatgc tcg                                           23

<210> SEQ ID NO 14
<211> LENGTH: 23
<212> TYPE: DNA

```
<213> ORGANISM: Artificial Sequence
<220> FEATURE:
<223> OTHER INFORMATION: (primer)

<400> SEQUENCE: 14
atgaaacaaa tgaatgatgc tct                                            23

<210> SEQ ID NO 15
<211> LENGTH: 23
<212> TYPE: DNA
<213> ORGANISM: Artificial Sequence
<220> FEATURE:
<223> OTHER INFORMATION: (probe)

<400> SEQUENCE: 15
aatgaatgat gctcatcatg gtg                                            23

<210> SEQ ID NO 16
<211> LENGTH: 12
<212> TYPE: DNA
<213> ORGANISM: Artificial Sequence
<220> FEATURE:
<223> OTHER INFORMATION: (primer)

<400> SEQUENCE: 16
gaatgatgct cg                                                        12

<210> SEQ ID NO 17
<211> LENGTH: 12
<212> TYPE: DNA
<213> ORGANISM: Artificial Sequence
<220> FEATURE:
<223> OTHER INFORMATION: (primer)

<400> SEQUENCE: 17
gaatgatgct ct                                                        12
```